United States Patent [19]

Los

[11] Patent Number: 4,544,754

[45] Date of Patent: Oct. 1, 1985

[54] PREPARATION OF IMIDAZOLINYL BENZOIC ACIDS, ESTERS AND SALTS

[75] Inventor: Marinus Los, Pennington, N.J.

[73] Assignee: American Cyanamid Company, Stamford, Conn.

[21] Appl. No.: 279,886

[22] Filed: Jul. 2, 1981

Related U.S. Application Data

[60] Division of Ser. No. 74,940, Sep. 13, 1979, Pat. No. 4,297,128, which is a division of Ser. No. 914,244, Jun. 9, 1978, Pat. No. 4,188,487, which is a continuation-in-part of Ser. No. 822,458, Aug. 8, 1977, abandoned.

[51] Int. Cl.$^4$ .............................................. C07D 233/70
[52] U.S. Cl. .................................................. 548/301
[58] Field of Search ........................................ 548/301

[56] References Cited

U.S. PATENT DOCUMENTS 3,867,394  2/1975  Sulkowski ........................... 546/271
4,041,045  8/1977  Los ...................................... 548/302

OTHER PUBLICATIONS

Smith, P. A. S., The Chemistry of Open-Chain Organic Nitrogen Compounds, vol. I, W. A. Benjamin, New York, 1965, pp. 142–143.

*Primary Examiner*—Richard A. Schwartz
*Attorney, Agent, or Firm*—H. G. Jackson

[57] ABSTRACT

The invention relates to novel imidazolinyl benzoic acids, esters and salts, a method for the preparation of the compounds and methods for controlling undesirable plant species therewith.

3 Claims, No Drawings

PREPARATION OF IMIDAZOLINYL BENZOIC ACIDS, ESTERS AND SALTS

This is a division of application Ser. No. 74,940, filed Sept. 13, 1979, now U.S. Pat. No. 4,297,128, which is a Division of Ser. No. 914,244 filed June 9, 1978 now U.S. Pat. No. 4,188,487, which is a continuation-in-part of Ser. No. 822,458 filed Aug. 8, 1977, now abandoned.

The invention is imidazolinyl benzoic acids, esters and salts represented by formula (I):

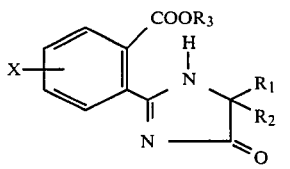

wherein X is hydrogen, alkyl $C_1-C_3$, halogen or nitro; $R_1$ is alkyl $C_1-C_4$; $R_2$ is alkyl $C_1-C_6$, cycloalkyl $C_3-C_6$, alkenyl $C_2-C_4$, phenyl, halophenyl or benzyl or when $R_1$ and $R_2$ are taken together with the carbon to which they are attached they may represent cycloalkyl $C_3-C_6$ optionally substituted with methyl; $R_3$ is hydrogen, alkyl $C_1-C_{12}$ optionally substituted with one $C_1-C_3$ alkoxy group or one $C_3-C_6$ cycloalkyl group or one phenyl group or one furyl group or with one to three halogen substituent(s) preferably chlorine, alkenyl $C_3-C_5$ optionally substituted with one or two $C_1-C_3$ alkyl group(s) or one phenyl group or with one to two halogen substituent(s) preferably chlorine, alkynyl $C_3-C_5$ optionally substituted with one or two $C_1-C_3$ alkyl group(s) or one phenyl group or with one to two halogen substituent(s) preferably chlorine, benzyl, cyclohexenylmethyl, ethynylcyclohexyl, ethynylalkyl, pentadienyl or cycloalkyl $C_3-C_6$ optionally substituted with one or two $C_1-C_3$ alkyl group(s) or a salt forming cation of alkali metals, ammonium and aliphatic ammonium; and when $R_1$ and $R_2$ are not the same the optical isomers and the isomeric mixtures thereof; and except when $R_3$ is a salt-forming cation, the acid addition salts thereof.

The invention also relates to a method controlling undesirable plant species with imidazolinyl benzoates comprising applying to the foliage of the undesirable plant species or to soil containing seeds, seedlings, or propagating organs of the undesirable plant species, a herbicidally effective amount of an imidazolinyl benzoate compound depicted by formula I above.

The invention further relates to a method for the preparation of the formula I imidazolinyl benzoates.

Preferred compounds for use as herbicidal agents are those represented by formula I above, wherein X is hydrogen, alkyl $C_1-C_3$ or halogen; $R_1$ is alkyl $C_1-C_3$; $R_2$ is alkyl $C_1-C_3$ or cyclohexyl, and when $R_1$ and $R_2$ are taken together with the carbon to which they are attached they represent cyclohexyl or methylcyclohexyl; $R_3$ is hydrogen, alkyl $C_1-C_{12}$ optionally substituted with one $C_1-C_3$ alkoxy group or one $C_3-C_6$ cycloalkyl group or one phenyl group or one furyl group or with one to three halogen substituent(s) preferably chlorine, alkenyl $C_3-C_5$ optionally substituted with one or two $C_1-C_3$ alkyl group(s) or one phenyl group or with one to two halogen substituent(s) preferably chlorine, alkynyl $C_3-C_5$ optionally substituted with one or two $C_1-C_3$ alkyl group(s) or one phenyl group or with one to two halogen substituent(s) preferably chlorine, benzyl, cyclohexenylmethyl, ethynylcyclohexyl, ethynylalkyl, pentadienyl or cycloalkyl $C_3-C_6$ optionally substituted with one or two $C_1-C_3$ alkyl group(s); or a salt forming cation of alkali metals and ammonium; and when $R_1$ and $R_2$ are not the same the optical isomers and the isomeric mixtures thereof; and except when $R_3$ is a salt-forming cation, the acid addition salts thereof.

Still more preferred formula (I) compounds are those wherein $R_1$ is methyl; $R_2$ is isopropyl; and the compounds may be grouped as follows:

a. wherein X is hydrogen or chlorine; $R_3$ is hydrogen; the alkali metal and ammonium salts thereof; the optical isomers thereof, and the isomeric mixtures thereof;

b. wherein X is hydrogen, methyl or chlorine; $R_3$ is alkyl $C_1-C_{12}$ optionally substituted with one $C_1-C_3$ alkoxy group or one $C_3-C_6$ cycloalkyl group or one phenyl group or one furyl group or with one to three halogen substituent(s) preferably chlorine; the optical isomers thereof, and the isomeric mixtures thereof, and the acid addition salts thereof;

c. wherein X is hydrogen, methyl or chlorine; $R_3$ is alkenyl $C_3-C_5$ optionally substituted with one or two $C_1-C_3$ alkyl group(s) or one phenyl group or with one to two halogen substituent(s) preferably chlorine; the optical isomers thereof, and the isomeric mixtures thereof, and the acid addition salts thereof;

d. wherein X is hydrogen, methyl or chlorine; $R_3$ is alkynyl $C_3-C_5$ optionally substituted with one or two $C_1-C_3$ alkyl group(s) or one phenyl group or with one to two halogen substituent(s) preferably chlorine; the optical isomers thereof, and the isomeric mixtures thereof, and the acid addition salts thereof.

In accordance with this invention, formula I imidazolinyl benzoates wherein $R_3$ is not H can be prepared by reacting an imidazoisoindoledione represented by formula II with an appropriate alkali metal alkoxide. The reaction is preferably conducted under a blanket of inert gas at a temperature between 20° C. and 50° C. Generally, an alkali metal or alkali metal hydride is mixed with an appropriate alcohol and the mixture then admixed with the imidazoisoindoledione II.

Among the inert gases which may be used to blanket these reactions are nitrogen, argon and helium; but nitrogen is preferred.

Alkali metals and alkali metal hydrides which may be used include sodium, sodium hydride, potassium, potassium hydride, lithium and lithium hydride.

These reactions may be graphically illustrated as follows:

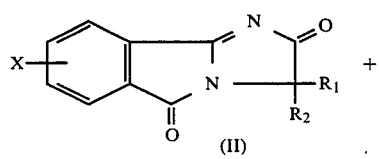

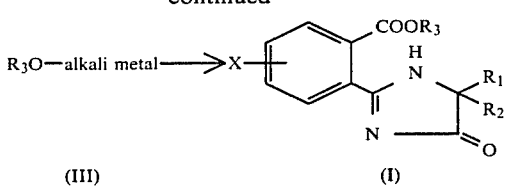

wherein X, $R_1$, $R_2$ and $R_3$ are as described above.

In these reactions, the alcohol functions as both reactant and solvent. As such, a secondary solvent is not required; however, when an expensive alcohol is used in the reaction and/or a large excess of alcohol would normally be required to provide optimum reaction conditions, it may be desirable to add a less expensive secondary solvent such as dioxane, tetrahydrofuran or other non-protic solvent, to the reaction mixture. The amount of non-protic solvent added to the reaction mixture may be widely varied in this way; however, it generally will not exceed fourfold the amount of alcohol used. Thus, the ratio of secondary solvent to alcohol, which may be employed in the process of the present invention, is from 0.0:1 to 4.0:1.

Formula I compounds, wherein $R_3$ is hydrogen are prepared by reacting a formula II imidazoisoindoledione with an excess of hydrochloric acid in the presence of a watermiscible solvent such as tetrahydrofuran or dioxane. This reaction yields the formula IV lactone hydrochloride which, when treated with one equivalent of base such as sodium hydroxide, potassium hydroxide or sodium carbonate, yields the corresponding acid. This reaction can be illustrated as follows:

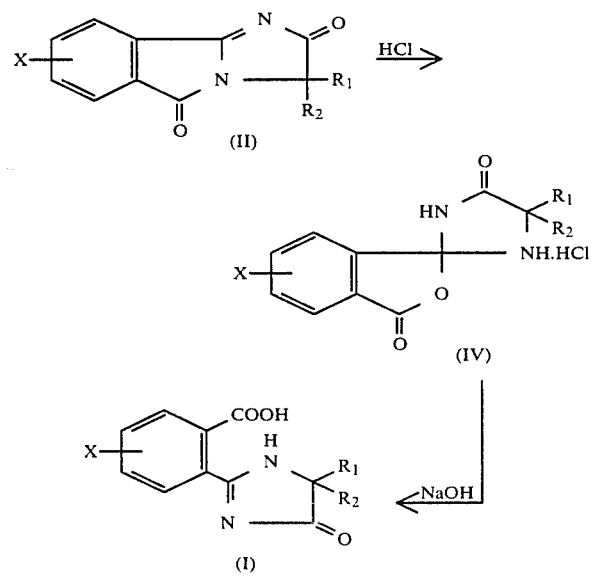

The thus-formed imidazolinyl acid can then be converted to the corresponding alkali metal, ammonium or aliphatic ammonium salt.

Where the alkali metal salt is desired, the acid is treated with a concentrated aqueous solution of the alkali metal hydroxide, followed by removal of the water, preferably through azeotropic distillation with an organic solvent such as dioxane.

The ammonium or aliphatic ammonium salts prepared in similar fashion excepting that the formula I acid is partially dissolved in a lower alcohol such as methanol, ethanol, isopropanol, or the like, and the thus-formed solution treated with ammonia or the appropriate aliphatic amine. Thereafter, the reaction mixture is concentrated and the remaining solid treated with hexane and then dried to recover the ammonium or aliphatic ammonium formula I salt.

The term, "aliphatic ammonium," means an aliphatic ammonium group of monoalkylammonium, dialkylammonium, trialkylammonium, monoalkenylammonium, dialkenylammonium, trialkenylammonium, monoalkynylammonium, dialkynylammonium, trialkynylammonium, monoalkanolammonium, dialkanolammonium, or trialkanolammonium, and the aliphatic ammonium group containing from 1 to 18 carbon atoms.

The aliphatic ammonium salts of the compounds of the invention are prepared from organic amines having a molecular weight below about 300. These amines include methylamine, ethylamine, n-propylamine, isopropylamine, n-butylamine, isobutylamine, sec-butylamine, n-amylamine, iso-amylamine, hexylamine, heptylamine, octylanine, nonylamine, decylamine, undecylamine, dodecylamine, tridecylamine, tetradecylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-amylamine, diisoamylamine, dihexylamine, diheptylamine, dioctylamine, trimethylamine, triethylamine, tri-n-propylamine, triisopropylamine, tri-n-butylamine, triisobutylamine, tri-sec-butylamine, tri-n-amylamine, ethanolamine, n-propanolamine, isopropanolamine, diethanolamine, N,N-diethylethanolamine, N-ethylpropanolamine, N-butylethanolamine, allylamine, n-butenyl-2-amine, n-pentenyl-2-amine, 2,3-dimethylbutenyl-2-amine, di-butenyl-2-amine, n-hexenyl-2-amine and propylenediamine.

The compounds represented by formula (I) above may be mixtures of two position isomers when X is other than hydrogen, since the intermediate imidazoisoindolediones of formula (II) are also mixtures of isomers when X is not hydrogen. As shown below, the compounds of formula (II) may be prepared from the corresponding phthalimidocarboxamide precursors by cyclizing same, and that cyclization occurs at either imide carbonyl group giving rise to an isomeric mixture when X is other than hydrogen:

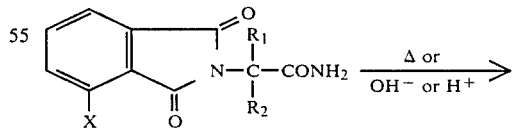

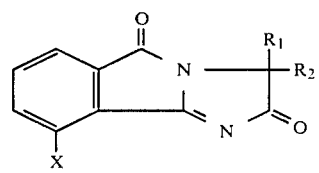

and

-continued

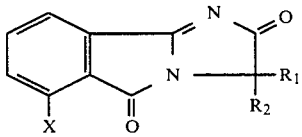

wherein $R_1$, $R_2$ and X are as defined above, excepting that X cannot be hydrogen.

It should also be understood that the imidazolinyl benzoates represented by formula I above, may be tautomeric. While for convenience, they are depicted by a single structure identified as formula I, they may exist in either of the isomeric forms illustrated as follows:

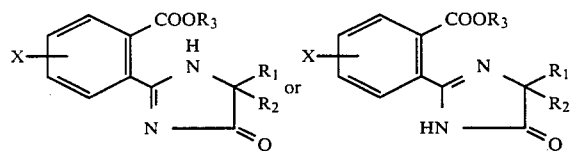

wherein X, $R_1$, $R_2$ and $R_3$ are as described. As such, both isomeric forms of the imidazolinyl benzoates are meant to be included under the formula I definition.

These compounds are amphoteric. They will dissolve in both acidic and basic aqueous solutions and when treated with strong acids, particularly strong mineral acids such as hydrochloric acid, sulfuric acid or hydrobromic acid, will form the acid addition salts of the imidazolinyl benzoates I.

It should also be understood that when $R_1$ and $R_2$ represent different groups on the imidazolinyl benzoates, depicted by formula I, the carbon atom to which they are attached is an asymmetric carbon atom. Therefore, the products (as well as their intermediates) exist in d- and l-forms as well as dl-forms.

Preparation of the d- or the l-form is thus readily obtained by reacting the appropriate optically active d- or l-imidazoisoindoledione II with the appropriate alcohol III to obtain the corresponding d- or l-imidazolinyl benzoate I.

The formula II imidazoisoindolediones II which are used as intermediates for the preparation of the imidazolinyl benzoates of this invention are described in my U.S. Pat. No. 4,017,510, issued Apr. 12, 1977.

The compounds of this invention are highly effective herbicidal agents useful for the control of both monocotyledonous, sedge (cyperaceous) and dicotyledonous plants. They may be employed for the postemergence control of undesirable plant species by applying a herbicidally effective amount thereof to the foliage of the plants, or they may be used for the preemergence control of the undesirable plants by applying a herbicidally effective amount of the active compound to soil containing seeds, seedlings or propagating organs, of the undesirable plants. Since the imidazolinyl benzoates (I) of the present invention exhibit very limited solubility in water, they are generally formulated as wettable powders, emulsifiable concentrates, or flowable liquids which are usually dispersed in water or other inexpensive liquid diluent for application as a liquid spray. The compounds of the invention may also be prepared as granular formulations containing, generally, about 10% to 15% by weight of toxicant.

Typically, a wettable powder can be prepared by grinding together about 25% to 80% by weight of the imidazolinyl benzoate, about 2% to 5% by weight of a surfactant such as sodium N-methyl-N-oleoyl taurate, alkyl phenoxy polyoxyethylene ethanol, or sodium alkyl naphthalene sulfonate, 5% to 10% by weight of a dispersing agent such as a highly purified sodium lignosulfonate and 25% to 63% by weight of a finely divided carrier such as kaolin, attapulgite, diatomaceous earth, or the like.

A typical formulation prepared in accordance with the above description is as follows:

50% by weight of 2-propynyl o-(5-isopropyl-5-methyl-4-oxo-2-imidazolin-2-yl)benzoate, 3% by weight of sodium N-methyl-N-oleoyl taurate, 10% by weight of sodium lignosulfonate, and 37% by weight of kaolin.

Flowable liquid formulations can be prepared by grinding together about 40% to 60% by weight of the formula I imidazolinyl benzoate, 2% to 3% by weight of the sodium salt of condensed naphthalene sulfonic acid, 2% to 3% by weight of a gelling clay, 2% by weight of propylene glycol, and from 54% to 32% by weight of water.

A typical granular formulation can be prepared by dissolving or dispersing the active compound in a solvent and applying the toxicant to a sorptive or non-sorptive carrier such as attapulgite, corn cob grits, pumice, talc, or the like.

As indicated above, the imidazolinyl compounds, depicted by formula I, are effective preemergence herbicides. They are highly effective for the control of broadleaf weeds and grass plants when applied at a rate of from about 0.07 kg per hectare to 11.2 kg per hectare to soil containing seeds, seedlings or propagating organs of the broadleaf weeds, sedges, or grass plants.

The compounds of the invention are also effective for the control of broadleaf weeds, sedges, and grass plants when applied at the rate of from about 0.28 kg per hectare to 11.2 kg per hectare to the foliage of the plants.

While the compounds of this invention are very effective for controlling a wide variety of plant species, they are unique among herbicides in their ability to control certain cyperaceous plants, particularly sedges, at relatively low rates of application. In practice, the formula I compounds have been found to be most effective as sedge control agents when applied as a preemergence application at rates of from 0.14 kg per hectare to 11.2 kg per hectare. It is, of course, recognized that higher rates of application of the formula I compounds can be used for sedge and other perennial plant control when infestations of the cyperacae or perennial plants are especially heavy. Under such conditions, the formula I imidazolinyl benzoates may be applied, preemergence or postemergence, at rates as high as 25 kg per hectare.

Among the cyperacae which can be controlled with the imidazolinyl benzoates of this invention are purple nutsedge (*Cyperus rotundus* L.), yellow nutsedge (*Cyperus esulentus* L.), false nutsedge (*Cyperus strigosus*) and the flat sedges, umbrella plants and kyllinga.

This invention is further illustrated by the following examples:

EXAMPLE 1

Preparation of 2-Propynyl o-(5-isopropyl-5-methyl-4-oxo-2-imidazolin-2-yl)benzoate.

To 12.5 ml of propargyl alcohol is added 0.1 g of a 50% suspension of sodium hydride in mineral oil. The addition is made under a blanket of nitrogen while the mixture is stirred and the temperature thereof maintained at from 20° C. to 25° C. by means of external cooling. The formation of the sodium salt of propargyl alcohol is complete in about 1 to 2 hours. To this solution is added 5.0 g of 3-isopropyl-3-methyl-5H-imidazo[2,1-a]isoindole-2(3H), 5-dione and the mixture stirred at room temperature overnight under a blanket of nitrogen. Thin layer chromatography indicates incomplete reaction and an additional 50 mg of a 50% suspension of sodium hydride in oil is added to the reaction mixture. After stirring overnight, the mixture is cooled to 5° C. and 0.7 ml of 3N hydrochloric acid is added. The mixture is then diluted with methylene chloride, washed with water and the organic phase dried and concentrated in vacuo. The crystalline residue is transferred to a filter funnel with hexane and air dried to give 6.02 g of 2-propynyl o-(5-isopropyl-5-methyl-4-oxo-2-imidazolin-2-yl)benzoate, melting point 131°–144° C. Material from a similar reaction was recrystallized from acetone-hexane to give pure product melting point 145°–147° C.

EXAMPLE 2

Preparation of Formula I Imidazolinyl Benzoates

The following imidazolinyl benzoates are prepared by essentially the same procedure as that described in Example 1, but substituting the appropriate alcohol for propargyl alcohol and the appropriate imidazoisoindoledione for 3-isopropyl-3-methyl-5H-imidazo[2,1-a]isoindole-2(3H), 5-dione. Graphically, the reaction may be illustrated as follows:

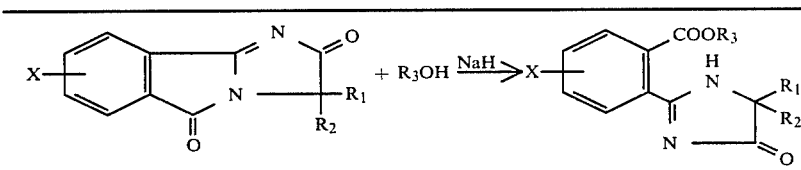

| $R_1$ | $R_2$ | $R_3$ | X | Melting Point °C. |
|---|---|---|---|---|
| $CH_3$ | $CH(CH_3)_2$ | $-CH_2CH_2CH_3$ | H | 120–121.5 (dec.) |
| $CH_3$ | $CH(CH_3)_2$ | $-CH_2C_6H_5$ | H | 110–113 (dec.) |
| $CH_3$ | $CH(CH_3)_2$ | $-(CH_2)_7CH_3$ | H | 73–75 (dec.) |
| $CH_3$ | $CH(CH_3)_2$ | $-(CH_2)_{11}CH_3$ | H | 62.5–64.5 (dec.) |
| $CH_3$ | $CH(CH_3)_2$ | $-CH_2CH=CH_2$ | H | 109–111.5 (dec.) |
| $CH_3$ | $CH(CH_3)_2$ | $-CH_3$ | H | 117–118 |
| $CH_3$ | $CH(CH_3)_2$ | $-C(CH_3)_2CH=CH_2$ | H | 115.5–117.5 |
| $CH_3$ | $CH(CH_3)_2$ | $-C(CH_3)_2C\equiv CH$ | H | 115–116 |
| $CH_3$ | $CH(CH_3)_2$ | $-CH(CH_3)_2$ | H | 121–122.5 |
| $CH_3$ | $CH(CH_3)_2$ | $-C(CH_3)_3$ | H | 139.5–141 |
| $CH_3$ | $CH(CH_3)_2$ | $-CH_2CH_3$ | H | 123–124.5 |
| $CH_3$ | $CH(CH_3)_2$ | $-CH(CH_3)C\equiv CH$ | H | 97–104 |
| $CH_3$ | $CH(CH_3)_2$ | $-CH_2C(Cl)=CH_2$ | H | 114–116 |
| $CH_3$ | $CH(CH_3)_2$ | $-CH_2CH_2C\equiv CH$ | H | 127–128 |
| $CH_3$ | $CH(CH_3)_2$ | $-CH(CH_3)CH=CH_2$ | H | 94–98 (dec.) |
| $CH_3$ | $-CH_2CH_2CH_3$ | $-C(CH_3)_2CH=CH_2$ | H | 103.5–107 (dec.) |
| $CH_3$ | cyclohexyl | $-C(CH_3)_2CH=CH_2$ | H | 115–120 (dec.) |
| $-(CH_2)_5-$ | | $-C(CH_3)_2CH=CH_2$ | H | 133.5–134.5 (dec.) |
| $-CH(CH_3)CH_2CH_2CH_2-$ | | $-CH_2C\equiv CH$ | H | 168–171 (dec.) |
| $-CH_3$ | $-CH(CH_3)_2$ | $-CH(CH_3)-C(CH_3)=CH_2$ | H | 85–94 (dec.) |
| $-CH_3$ | $-CH(CH_3)_2$ | $-CH_2CH=CHCH_3$ | H | 101–112 (dec.) |
| $-CH_3$ | $-CH(CH_3)_2$ | $-CH_2C(CH_3)=CH_2$ | H | 91–102 (dec.) |
| $-CH_3$ | $-CH(CH_3)_2$ | $-CH_2CH=C(CH_3)_2$ | H | 107–111 |
| $-CH_3$ | $-CH(CH_3)_2$ | $-CH_2-C_6H_5$ | H | 100–106 (dec.) |
| $-CH_3$ | $-CH(CH_3)_2$ | $-CH(CH=CH_2)_2$ | H | 78–87 (dec.) |
| $-CH_3$ | $-CH(CH_3)_2$ | $-CH(CH_3)-CH=CHCH_3$ | H | 89–107 (dec.) |
| $-CH(CH_3)_2$ | $-CH(CH_3)_2$ | $-CH_3$ | H | 146–147 |
| $-(CH_2)_5-$ | | $-CH_3$ | H | 164–165 |
| $CH_3$ | $CH(CH_3)_2$ | $-CH_2C(CH_3)_3$ | H | 147–148 |
| $CH_3$ | $CH(CH_3)_2$ | $-C_{18}H_{37}-n$ | H | 79–81.5 |
| $CH_3$ | $CH(CH_3)_2$ | $-CH_2CH_2OCH_3$ | H | 87.5–92.5 |
| $CH_3$ | $CH(CH_3)_2$ | $-CH_2-\text{furyl}$ | H | 122–125 |
| $CH_3$ | $CH(CH_3)_2$ | $-C_6H_{13}-n$ | H | 84–86 |

-continued $$X \underset{O}{\overset{N}{\underset{\|}{\bigcirc}}} \underset{R_2}{\overset{N}{\underset{R_1}{\bigcirc}}} + R_3OH \xrightarrow{NaH} X \underset{N}{\overset{COOR_3}{\underset{\|}{\bigcirc}}} \underset{O}{\overset{H}{\underset{R_2}{\bigcirc}}} R_1$$

| R₁ | R₂ | R₃ | X | Melting Point °C. |
|---|---|---|---|---|
| $CH_3$ | $CH(CH_3)_2$ | $-C(CH_3)(C_2H_5)CH_3$ | H | 87–89 |
| $CH_3$ | $CH(CH_3)_2$ | $-CH_2CH_2OC_2H_5$ | H | 99–100 |
| $CH_3$ | $CH(CH_3)_2$ | $-CH_2-CH=CH-C_6H_5$ | H | 120–125 |
| $CH_3$ | $CH(CH_3)_2$ | $-CH_2-C\equiv C-C_6H_5$ | H | 134.5–138 |
| $CH_3$ | $CH(CH_3)_2$ | $-CH_2-C\equiv C-CH_3$ | H | 125–128 |
| $CH_3$ | $CH(CH_3)_2$ | $-CH(CH_3)$-cyclopropyl | H | 95.98 |
| $CH_3$ | $CH(CH_3)_2$ | $-CH_2-C\equiv C-C_7H_{15}-n$ | H | 94–96.5 |
| $CH_3$ | $CH(CH_3)_2$ | $-CH_2CCl_3$ | H | 143–145 |
| $CH_3$ | $CH(CH_3)_2$ | $-C(C_2H_5)_2CH=CH_2$ | H | 111.5–115.5 |
| $CH_3$ | $CH(CH_3)_2$ | 2,5-dimethylcyclohexyl with $CH(CH_3)_2$ | H | 74–78 |
| $CH_3$ | $CH(CH_3)_2$ | 1-ethynylcyclohexyl | H | 168–169 |
| $CH_3$ | $CH(CH_3)_2$ | $-CH_2-C(Cl)=CH_2$ | 4(5) $CH_3$ | 128–130 |
| $CH_3$ | $CH(CH_3)_2$ | $-CH_3$ | 4(5) $CH_3$ | 143–151 |
| $CH_3$ | $CH(CH_3)_2$ | $-CH_2-C\equiv CH$ | 4(5) $CH_3$ | 154–159 |
| $CH_3$ | $CH(CH_3)_2$ | $-C(CH(CH_3)_2)(CH(CH_3)_2)CH=CH_2$ | H | 153–157.5 |
| $CH_3$ | $CH(CH_3)_2$ (+) isomer | $-C_2H_5$ | H | 106–108 |
| $CH_3$ | $CH(CH_3)_2$ (−) isomer | $-CH_2-C\equiv CN$ | H | 134–135 |
| $CH_3$ | $CH(CH_3)_2$ (+) isomer | $-CH_2-C(Cl)=CH_2$ | H | 120–122 |
| $CH_3$ | $CH(CH_3)_2$ | $-CH(CH_3)CH=CHCH_3$ | 4(5) $CH_3$ | 95–111 |
| $CH_3$ | $CH(CH_3)_2$ | $-CH_3$ | 3(6) Cl | 162–166 |
| $CH_3$ | $CH(CH_3)_2$ | $-CH_2-C\equiv CH$ | 3(6) Cl | 164–166 |
| $CH_3$ | $CH(CH_3)_2$ | $-CH_2-C\equiv C-CH_2OH$ | H | 132–134 |
| $CH_3$ | $CH(CH_3)_2$ | $-CH_2-C(Cl)=CH_2$ | 3(6) Cl | 154–160 |
| $CH_3$ | $CH(CH_3)_2$ | $-CH_2-CH_2-$ | H | 166–169 |
| $CH_3$ | $CH(CH_3)_2$ | $-CH(CH_3)CH=CH-CH_3$ | 3(6) Cl | 161–163 |
| $CH_3$ | $CH(CH_3)_2$ | $-C_2H_5$ | 3(6) $NO_2$ | 156–157 |
| $CH_3$ | $C_2H_5$ | $-CH_3$ | H | 135–136 |
| $CH_3$ | $C_2H_5$ | $-CH_2-C\equiv CH$ | H | 137–138 |

-continued

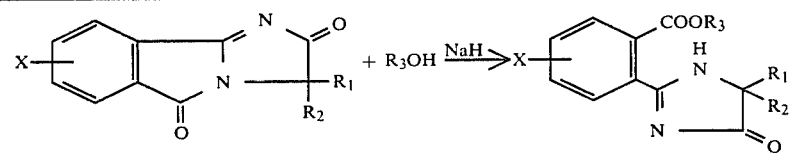

| R₁ | R₂ | R₃ | X | Melting Point °C. |
|---|---|---|---|---|
| CH₃ | C₂H₅ | —CH₂—C(Cl)=CH₂ | H | 125–126 |
| CH₃ | CH(CH₃)₂ | —CH₂—C(Cl)=CHCl | H | 107–114 |
| CH₃ | C₂H₅ | —CH(CH₃)CH=CHCH₃ | H | 119–121 |
| CH₃ | CH(CH₃)₂ | —CH₂—C(Cl)=CH₂ | 3(6) NO₂ | 161–162 |
| CH₃ | CH(CH₃)₂ | —C(CH₃)(C₂H₅)—CH=CH₂ | H | 73–79 |
| CH₃ | C₂H₅ | —C(CH₃)₂—CH=CH₂ | H | 127–128 |
| CH₃ | CH(CH₃)₂ | —C(CH(CH₃)₂)₂—C≡CH | H | 122–122.5 |
| CH₃ | CH(CH₃)₂ | —C₂H₅ | 4(5) Cl | 112–138 |
| C₂H₅ | CH(CH₃)₂ | —CH₃ | H | 139–140 |
| C₂H₅ | CH(CH₃)₂ | —CH₂—C≡CH | H | 147–149 |
| C₂H₅ | CH(CH₃)₂ | —CH₂—C(Cl)=CH₂ | H | 134–135 |
| CH₃ | CH(CH₃)₂ | —CH₂—C≡CH | 4(5) Cl | 177–187 |
| CH₃ | CH(CH₃)₂ | —CH(CH₃)CH=CHCH₃ | 4(5) Cl | oil |
| CH₃ | CH(CH₃)₂ | —CH₂—C(Cl)=CH₂ | 4(5) Cl | oil |
| CH₃ | CH(CH₃)₂ | —CH(CH=CH₂)—C≡CH | H | oil |
| CH₃ | CH(CH₃)₂ | —C(CH₃)₂—CH=CH₂ | 4(5) Cl | oil |
| CH₃ | CH(CH₃)₂ | H | 4(5) Cl | 177–179 |
| CH₃ | C₂H₅ | H | H | 195–197 |
| C₂H₅ | CH(CH₃)₂ | H | H | 179–180 |
| CH₃ | CH(CH₃)₂ | H | 3(6) Cl | 154–156 |
| CH₃ | CH(CH₃)₂ | C₂H₅ | 4(5) CH₃ | |
| CH₃ | CH(CH₃)₂ | C₃H₇—n | 4(5) CH₃ (4 or 5) | |
| CH₃ | CH(CH₃)₂ | C₃H₇—n | 4(5) CH₃ (4 or 5) | |
| CH₃ | CH(CH₃)₂ | C₃H₇—n | 4(5) CH₃ (4 and 5) | |
| CH₃ | CH(CH₃)₂ | CH(CH₃)₂ | 4(5) CH₃ | |

EXAMPLE 3

Preparation of 1,1-Dimethylallyl o-(5-isopropyl-5-methyl-4-oxo-2-imidazolin-2-yl)benzoate hydrochloride

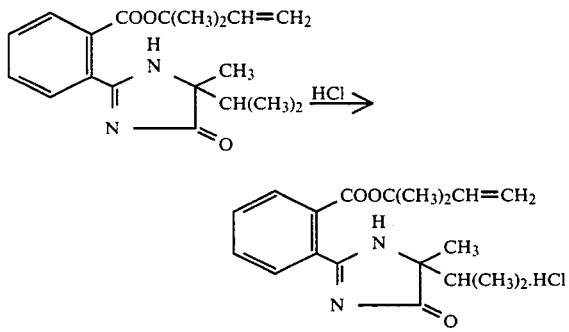

To a solution containing 164 mg. 1,1-dimethylallyl o-(5-isopropyl-5-methyl-4-oxo-2-imidazolin-2-yl)benzoate (0.5 mmol) in 5 ml methylene chloride and 5 ml absolute ethanol is added 0.5 ml 1.0N hydrochloric acid. The mixture is concentrated in vacuo and the residue treated with ether to give a crystalline product which is removed by filtration, washed with ether and air dried to give 170 mg hydrochloride salt, melting point 259°–262° C. (decomp.). The melting point of this and other salts is dependent upon the rate of heating.

EXAMPLE 4

Preparation of o-(5-Isopropyl-5-methyl-4-oxo-2-imidazolin-2-yl)benzoic acid

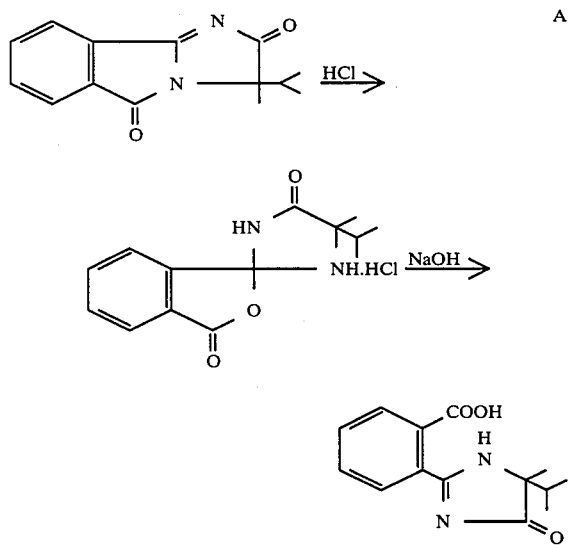

To a stirred solution containing 5 g of 3-isopropyl-3-methyl-5H-imidazo[2,1-a]isoindole-2(3H),5-dione in 15 ml dioxane is added a mixture of 10 ml concentrated hydrochloric and 10 ml water. The mixture is heated to the boiling point and then allowed to cool to room temperature. The crystalline solid is removed by filtration, washed with water, acetone and air dried. The filtrate is concentrated in vacuo, the solid washed with acetone and air-dried. Thus, in two crops, a total of 4.5 g of the lactone hydrochloride, represented by structure A, is obtained, melting point 265° C. (decomp.).

To a stirred, partial solution of the hydrochloride salt (4.5 g) in 30 ml water is added a solution containing 0.6 g sodium hydroxide in 10 ml water. Complete solution occurs in a few minutes, and after approximately 15 minutes a solid separates from the solution. This is removed by filtration. The filtrate is concentrated in vacuo, the solid removed by filtration, combined with the first solid, washed with water and air-dried to give 3.8 g of o-(5-isopropyl-5-methyl-4-oxo-2-imidazolin-2-yl)benzoic acid, melting point 162°–163° C. The analytically pure sample had melting point 163°–165° C.

EXAMPLE 5

Salts of o-(5-Isopropyl-5-methyl-4-oxo-2-imidazolin-2-yl)-benzoic acid

The sodium salt is prepared by adding with stirring 9.9 ml 1N sodium hydroxide to a partial solution of 2.58 g imidazolinyl acid in 10 ml water. After 1.5 hours, the solution is concentrated in vacuo and the remaining water then removed azeotropically with dioxane to give the hydroscopic sodium salt, melting point 184°–188° C.

Amine salts are simply made in methanol. Thus, to a stirred, partial solution of 5.0 g imidazolinyl acid in 15 ml methanol is added 3.17 ml triethylamine. After 0.75 hour, a clear solution is obtained. The solution is concentrated and the residual slurry diluted with hexane, filtered and dried to give the triethylamine salt, melting point 54°–55° C. The isopropylamine salt prepared similarly has melting point 92°–98° C.

EXAMPLE 6

Postemergence Herbicidal Activity

The postemergence herbicidal activity of the compounds of the invention is demonstrated by the following tests, wherein a variety of monocotyledonous, cyperaceous and dicotyledonous plants are treated with test compounds dispersed in aqueous acetone mixtures. In the tests, seedling plants are grown in separate cups for about 2 weeks. The test compounds are dispersed in 50/50 acetone/water mixtures containing 0.5% TWEEN ®20, a polyoxyethylene sorbitan monolaurate surfactant of Atlas Chemical Industries, in sufficient quantity to provide the equivalent of about 0.07 kg to 11.2 kg per hectare of active compound when applied to the plants through a spray nozzle operating at 2.8 kg/Cu$^2$ pressure for a predetermined time. After spraying, the plants are placed on greenhouse benches and are cared for in the usual manner, commensurate with conventional greenhouse practices. Two weeks after treatment, the seedling plants, with the exception of wild oats which are rated at 5 weeks, are examined and rated according to the rating system provided below. The data obtained are reported in Table I below.

| Rating System: | % Difference in Growth from the Check* |
|---|---|
| 0 - No effect | 0 |
| 1 - Possible effect | 1–10 |
| 2 - Slight effect | 11–25 |
| 3 - Moderate effect | 26–40 |
| 5 - Definite injury | 41–60 |
| 6 - Herbicidal effect | 61–75 |
| 7 - Good herbicidal effect | 76–90 |

-continued

| Rating System: | % Difference in Growth from the Check* |
|---|---|
| 8 - Approaching complete kill | 91-99 |
| 9 - Complete kill | 100 |
| 4 - Abnormal growth; that is, a definite physiological malformation but with an over-all effect less than a 5 on the rating scale. | |

*Based on visual determination of stand, size, vigor, chlorosis, growth malformation and over-all plant appearance.

Plant abbreviations

PN—Purple Nutsedge (*Cyperus rotundus* L.)
SE—Sesbania (*Sesbania exaltata*)
MU—Mustard (*Brassica kaber*)
PI—Pigweed (*Amaranthus retroflexus*)
RW—Ragweed (*Ambrosia artemisiifolia*)
MG—Morningglory (*Ipomoea purpurea*)
BA—Barnyardgrass (*Echinochloa crusgalli*)
CR—Crabgrass (*Digitaria sanguinalis*)
FO—Green Foxtail (*Setaria viridis*)
WO—Wild Oats (*Avena fatua*)
TW—Teaweed (*Sida spinosa*)
VL—Velvetleaf (*Abutilon theophrasti*)
CN—Corn (*Zoa mays*)
CO—Cotton (*Gossypium hirsutum*)
SY—Soybean (*Glycine max*)
RI—Rice (*Oryza sativa*)
JW—Jimsonweed (*Datura stramonium* L.).

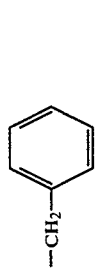

TABLE I-continued
Postemergence Herbicidal Activity for Compounds having the Structure:

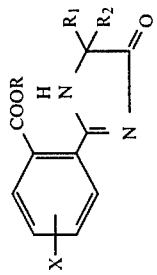

| | | Structure | | Rate kg per | | | | | | | | Plant Species | | | | | | | | | |
|---|---|---|---|---|---|---|---|---|---|---|---|---|---|---|---|---|---|---|---|---|---|
| $R_1$ | $R_2$ | | $R_3$ | X | Hectare | PN | SE | MU | PI | RW | MG | TW | VL | BA | CR | FO | WO | CN | CO | SY | RI |
| CH$_3$ | —CH(CH$_3$)$_2$ | | —C(CH$_3$)$_2$C≡CH HCl salt | H | 11.2 | 7 | 7 | 9 | 9 | 9 | 9 | 8 | 9 | 8 | 9 | 9 | 9 | — | — | — | — |
| | | | | | 4.48 | 3 | 9 | 9 | 9 | 7 | 9 | 9 | 9 | 3 | 2 | 6 | 9 | 9 | 9 | 8 | 6 |
| | | | | | 1.12 | 2 | 2 | 9 | 9 | 5 | 8 | — | 5 | 2 | 0 | 5 | 6 | 9 | 8 | 8 | 6 |
| | | | | | 0.56 | 2 | 2 | 9 | 9 | 0 | 9 | 0 | 8 | 0 | 0 | 3 | 3 | 9 | 8 | 8 | — |
| CH$_3$ | —CH(CH$_3$)$_2$ | | —CH(CH$_3$)C≡CH | H | 11.2 | 7 | 9 | 9 | 9 | 7 | 9 | 7 | 9 | 7 | 7 | 6 | 9 | — | — | — | — |
| CH$_3$ | —CH(CH$_3$)$_2$ | | —CH$_2$—C(Cl)=CH$_2$ | H | 11.2 | 9 | 9 | 9 | 9 | 9 | 9 | 8 | 9 | 9 | 9 | 9 | 9 | — | — | — | — |
| CH$_3$ | —CH(CH$_3$)$_2$ | | —CH$_2$CH$_2$C≡CH | H | 11.2 | 6 | — | 4 | 8 | 0 | 5 | 4 | 7 | 4 | 4 | 4 | 0 | — | — | — | — |
| CH$_3$ | —CH(CH$_3$)$_2$ | | —CH(CH$_3$)CH=CH$_2$ | H | 11.2 | 0 | 3 | 7 | 7 | 6 | 3 | 4 | 4 | 2 | 2 | 2 | 4 | — | — | — | — |
| CH$_3$ | —C(CH$_3$)$_2$— | | —C(CH$_3$)$_2$CH=CH$_2$ | H | 11.2 | 0 | 2 | 6 | 6 | 4 | 4 | 4 | 0 | 4 | 4 | 4 | 4 | — | — | — | — |
| —CH(CH$_3$)CH$_2$CH$_2$CH$_2$— | | | —CH$_2$C≡CH | H | 11.2 | 0 | 0 | 4 | 0 | 0 | 4 | 0 | 0 | 8 | 6 | 3 | 5 | — | — | — | — |
| CH$_3$ | —CH(CH$_3$)$_2$ | | —CH(CH$_3$)—C(CH$_3$)=CH$_2$ | H | 11.2 | 5 | 9 | 7 | 7 | 4 | 4 | 4 | 4 | 0 | 5 | 1 | 2 | — | — | — | — |
| CH$_3$ | —CH(CH$_3$)$_2$ | | —CH=CH=CHCH$_3$ | H | 11.2 | 2 | 2 | 6 | 6 | 6 | 6 | 3 | 5 | 5 | 3 | 2 | 2 | — | — | — | — |
| CH$_3$ | —CH(CH$_3$)$_2$ | | —CH$_2$C(CH$_3$)=CH$_2$ | H | 11.2 | 0 | 0 | 7 | 8 | 0 | 0 | 1 | 3 | 0 | 0 | 0 | 0 | — | — | — | — |
| CH$_3$ | —CH(CH$_3$)$_2$ | | —CH$_2$CH=C(CH$_3$)$_2$ | H | 11.2 | 3 | 5 | 7 | 7 | 0 | 6 | 5 | 6 | 2 | 5 | 3 | 3 | — | — | — | — |
| CH$_3$ | —CH(CH$_3$)$_2$ | | —CH$_2$-cyclohexenyl | H | 11.2 | 0 | 0 | 3 | 7 | 0 | 5 | 2 | 3 | 0 | 0 | 0 | 0 | — | — | — | — |
| CH$_3$ | —CH(CH$_3$)$_2$ | | —CH(CH=CH$_2$)$_2$ | H | 11.2 | 3 | 9 | 8 | 9 | 4 | 9 | 8 | 9 | 7 | 8 | 8 | 7 | — | — | — | — |
| CH$_3$ | —CH(CH$_3$)$_2$ | | —CH(CH$_3$)—CH=CHCH$_3$ | H | 11.2 | 3 | 7 | 9 | 9 | 2 | 8 | 7 | 9 | 6 | 5 | 7 | 5 | — | — | — | — |
| CH$_3$ | CH(CH$_3$)$_2$ | | —CH$_2$C(CH$_3$)$_3$ | H | 11.2 | 5 | 0 | 6 | 9 | 0 | 7 | 5 | 4 | 0 | 0 | 0 | 0 | — | — | — | — |
| CH$_3$ | CH(CH$_3$)$_2$ | | —CH$_2$CH$_2$OCH$_3$ | H | 11.2 | 2 | 0 | 9 | 9 | 7 | 0 | 6 | 8 | 4 | 0 | 4 | 8 | — | — | — | — |
| | | | | | 2.24 | 0 | | | | 0 | 5 | 6 | 7 | 0 | 0 | 0 | 1 | 6 | 8 | 8 | — |
| | | | | | 1.12 | 0 | | | | 0 | 5 | 3 | 8 | 0 | 0 | 0 | 0 | 0 | 5 | 5 | — |
| | | | | | 0.56 | 0 | | | | 0 | 3 | 0 | 8 | 0 | 0 | 0 | 0 | 0 | 2 | 3 | — |
| | | | | | 0.28 | 0 | | | | 0 | 3 | 0 | 0 | 0 | 0 | 0 | 0 | 0 | 2 | 1 | — |
| CH$_3$ | CH(CH$_3$)$_2$ | | —CH$_2$-furanyl | H | 11.2 | 8.5* | 8 | 9 | 9 | 6* | 9 | 8 | 9 | 9 | 9 | 9 | 9 | 7 | 7 | 9 | — |
| | | | | | 2.24 | 8 | | | | 7 | 9 | 9 | 9 | 7 | 5 | 9 | 9 | 8 | 8 | 9 | — |
| | | | | | 1.12 | 8 | | | | 8 | 9 | 9 | 9 | 6 | 3 | 7 | 9 | 7 | 9 | 9 | — |
| | | | | | 0.56 | 7 | | | | 3 | 8 | 8 | 9 | 3 | 0 | 6 | 7 | 7 | 8 | 9 | — |
| | | | | | 0.28 | 3 | | | | 2 | 6 | 7 | 9 | 2 | 0 | 0 | 2 | 7 | 7 | 8 | — |
| CH$_3$ | CH(CH$_3$)$_2$ | | —C$_6$H$_{11,n}$ | H | 11.2 | 2 | 0 | 3 | 9 | 0 | 5 | 4 | 4 | 0 | 0 | 0 | 1 | — | — | — | — |

TABLE I-continued

Postemergence Herbicidal Activity for Compounds having the Structure:

| R₁ | R₂ | Structure R₃ | X | Rate kg per Hectare | PN | SE | MU | PI | RW | MG | TW | VL | BA | CR | FO | WO | CN | CO | SY | RI |
|---|---|---|---|---|---|---|---|---|---|---|---|---|---|---|---|---|---|---|---|---|
| CH₃ | CH(CH₃)₂ | CH₃—C(CH₃)—C₂H₅ | H | 11.2<br>2.24<br>1.12 | 6*<br>3<br>2 | 0<br>  <br>  | 9<br>  <br>  | 9<br>  <br>  | 0<br>0<br>0 | 7<br>3<br>2 | 6<br>2<br>0 | 6<br>9<br>0 | 2<br>0<br>0 | 0<br>0<br>0 | 0<br>0<br>0 | 8<br>0<br>0 |   | 7<br>7<br>6 | 6<br>3<br>5 |   |
| CH₃ | CH(CH₃)₂ | —CH₂CH₂OC₂H₅ | H | 11.2<br>2.24<br>1.12<br>0.56 | 0<br>2<br>1<br>0 | 0<br>  <br>  <br>  | 7<br>  <br>  <br>  | 9<br>  <br>  <br>  | 0<br>2<br>0<br>0 | 4<br>7<br>7<br>2 | 5<br>8<br>5<br>2 | 6<br>9<br>3<br>2 | 4<br>2<br>0<br>0 | 0<br>0<br>0<br>0 | 0<br>0<br>0<br>0 | 4<br>0<br>0<br>0 | 5<br>2<br>0<br>0 | 7<br>7<br>6 | 6<br>3<br>5 |   |
| CH₃ | CH(CH₃)₂ | —CH₂—CH=CH— (phenyl) | H | 11.2<br>2.24<br>1.12<br>0.56 | 4.5*<br>8<br>7<br>8 | 7.5*<br>  <br>  <br>  | 7.5*<br>  <br>  <br>  | 8.5*<br>  <br>  <br>  | 2<br>3<br>2<br>2 | 5*<br>7<br>6<br>5 | 8.5*<br>7<br>2<br>2 | 9<br>9<br>2<br>7 | 5<br>7<br>2<br>0 | 5<br>2<br>0<br>0 | 6<br>7<br>3<br>0 | 3.5*<br>6<br>2<br>0 | 7<br>7<br>6 | 8<br>8<br>6 | 8<br>8<br>7 |   |
| CH₃ | CH(CH₃)₂ | —CH₂—C≡C— (phenyl) | H | 11.2 | 1.5* | 4 | 6.5* | 8* | 3* | 5.5* | 6* | 6.5* | 4 | 0 | 0 | 5.5* |   |   |   |   |
| CH₃ | CH(CH₃)₂ | —CH₂—C≡C—CH₃ | H | 11.2<br>2.24<br>1.12<br>0.56 | 4.5*<br>7<br>3<br>3 | 6.5*<br>  <br>  <br>  | 8.5*<br>  <br>  <br>  | 9<br>  <br>  <br>  | 7.5*<br>3<br>0<br>0 | 7.5*<br>8<br>8<br>7 | 8.5*<br>8<br>5<br>5 | 8.5*<br>9<br>9<br>9 | 7*<br>2<br>0<br>0 | 6.5*<br>0<br>0<br>0 | 8.5*<br>3<br>0<br>0 | 8.5*<br>8<br>2<br>0 | 9<br>8<br>7 | 8<br>8<br>8 | 9<br>9<br>9 |   |
| CH₃ | CH(CH₃)₂ | —CH(cyclopropyl)CH₃ | H | 11.2<br>2.24<br>1.12<br>0.56 | 6.5*<br>8<br>7<br>5 | 3<br>  <br>  <br>  | 9<br>  <br>  <br>  | 9<br>  <br>  <br>  | 5<br>0<br>0<br>0 | 7.5*<br>6<br>6<br>5 | 7<br>0<br>0<br>0 | 8.5*<br>8<br>0<br>0 | 4<br>0<br>0<br>0 | 4<br>0<br>0<br>0 | 4<br>7<br>0<br>0 | 8*<br>2<br>0<br>0 | 8<br>7<br>7 | 8<br>8<br>8 | 8<br>3<br>7 |   |
| CH₃ | CH(CH₃)₂ | —CH₂—C≡C—C₇H₁₅—n | H | 11.2<br>2.24<br>1.12<br>0.56 | 3<br>0<br>0<br>0 | 6<br>  <br>  <br>  | 8<br>  <br>  <br>  | 9<br>  <br>  <br>  | 3<br>0<br>0<br>0 | 6<br>6<br>5<br>3 | 7<br>2<br>0<br>0 | 9<br>9<br>0<br>6 | 3<br>0<br>0<br>0 | 0<br>0<br>0<br>0 | 8<br>0<br>0<br>0 | 5<br>2<br>0<br>0 | 3<br>3<br>3 | 7<br>5<br>5 | 7<br>5<br>5 |   |
| CH₃ | CH(CH₃)₂ | —CH₂CCl₃ | H | 11.2<br>2.24<br>1.12<br>0.56 | 2<br>6<br>6<br>3 | 9<br>  <br>  <br>  | 8<br>  <br>  <br>  | 9<br>  <br>  <br>  | 6<br>9<br>8<br>3 | 6<br>8<br>9<br>8 | 8<br>9<br>8<br>5 | 8<br>8<br>9<br>8 | 5<br>8<br>9<br>3 | 0<br>5<br>7<br>0 | 8<br>9<br>9<br>8 | 9<br>9<br>9<br>9 | 9<br>9<br>9 | 9<br>8<br>8 | 9<br>9<br>9 |   |

TABLE I-continued

Postemergence Herbicidal Activity for Compounds having the Structure:

$$\text{structure with COOR, NH, N, R}_1, \text{R}_2, \text{X substituents on phenyl ring}$$

| Structure | | | Rate | Plant Species | | | | | | | | | | | | | | | | |
|---|---|---|---|---|---|---|---|---|---|---|---|---|---|---|---|---|---|---|---|---|
| R₁ | R₂ | R₃ | X | kg per Hectare | PN | SE | MU | PI | RW | MG | TW | VL | BA | CR | FO | WO | CN | CO | SY | RI |
| CH₃ | CH(CH₃)₂ | —C(C₂H₅)₂CH=CH₂ | H | 0.28 | 2 | | | | 3 | 7 | 3 | 8 | 0 | 0 | 7 | 9 | 9 | 7 | 9 | |
| | | | | 0.14 | 0 | | | | 1 | 6 | 3 | 9 | 0 | 0 | 7 | 9 | 9 | 7 | 8 | |
| CH₃ | CH(CH₃)₂ | CH(CH₃)₂ cyclohexyl-CH₃ | H | 11.2 | 1 | 8 | 7 | 9 | 5 | 0 | 6 | 8 | 5 | 3 | 7 | 7 | 9 | 7 | 8 | |
| | | | | 2.24 | 7 | | | | 5 | 8 | 6 | 9 | 2 | 2 | 5 | 7 | 9 | 7 | 8 | |
| | | | | 1.12 | 1 | | | | 3 | 7 | 3 | 9 | 0 | 0 | 2 | 6 | 9 | 7 | 8 | |
| | | | | 0.56 | 1 | | | | 0 | 8 | 5 | 9 | 0 | 0 | 0 | 3 | 9 | 6 | 8 | |
| CH₃ | CH(CH₃)₂ | CH(CH₃)₂ cyclohexyl C≡CH | H | 11.2 | 0 | 5 | 9 | 9 | 6 | 6 | 6 | 3 | 2 | 9 | 5 | 0 | 7 | 0 | 5 | |
| | | | | 2.24 | 0 | | | | 0 | 5 | 3 | 0 | 0 | 0 | 0 | 0 | 3 | 0 | 3 | |
| | | | | 1.12 | 0 | | | | 0 | 2 | 0 | 0 | 0 | 0 | 0 | 0 | 3 | 0 | | |
| CH₃ | CH(CH₃)₂ | Cl—CH₂—C—CH₂ | H | 11.2 | 0 | 0 | 8 | 9 | 0 | 6 | 0 | 3 | 0 | 0 | 0 | 0 | | | | |
| CH₃ | CH(CH₃)₂ | —CH₂—C—CH₂ with Cl | 4(5)CH₃ | 11.2 | 2 | 7 | 9 | 9 | 8 | 7 | 9 | 9 | 8 | 8 | 8 | 9 | 9 | 3 | 7 | |
| | | | | 2.24 | 0 | | | | 8 | 6 | 5 | 9 | 6 | 5 | 7 | 9 | 9 | 2 | 7 | |
| | | | | 1.12 | 0 | | | | 7 | 3 | 3 | 9 | 2 | 0 | 6 | 9 | 7 | 2 | 6 | |
| | | | | 0.56 | 0 | | | | 3 | 2 | 2 | 8 | 0 | 0 | 1 | 9 | 7 | 2 | 5 | |
| | | | | 0.28 | 0 | | | | 2 | 0 | 0 | 7 | 0 | 9 | 0 | 9 | 3 | 2 | | |
| CH₃ | CH(CH₃)₂ | —CH₃ | 4(5)CH₃ | 11.2 | 2 | 7 | 9 | 3 | 7 | 7 | 8 | 9 | 8 | 2 | 8 | 8 | 3 | 3 | 8 | |
| | | | | 2.24 | 0 | | | | 2 | 2 | 3 | 8 | 0 | 0 | 2 | 2 | 3 | 2 | 7 | |
| CH₃ | CH(CH₃)₂ | —CH₂—C≡CH | 4(5)CH₃ | 11.2 | 3 | 8 | 9 | 9 | 8 | 7 | 8 | 9 | 8 | 9 | 9 | 9 | 9 | 5 | 9 | |
| | | | | 2.24 | 3 | | | | 9 | 7 | 5 | 9 | 8 | 6 | 6 | 9 | 9 | 5 | 7 | |
| | | | | 1.12 | 0 | | | | 9 | 3 | 3 | 9 | 2 | 2 | 6 | 9 | 9 | 5 | 7 | |
| | | | | 0.56 | 0 | | | | 3 | 3 | 3 | 8 | 0 | 0 | 3 | 9 | 9 | 5 | 7 | |
| | | | | 0.28 | 0 | | | | 3 | 0 | 0 | 8 | 0 | 0 | 3 | 9 | 9 | 2 | 6 | |
| | | | | 0.14 | 0 | | | | 2 | 0 | 0 | 6 | 0 | 0 | 0 | 9 | 7 | 0 | 5 | |

TABLE I-continued

Postemergence Herbicidal Activity for Compounds having the Structure:

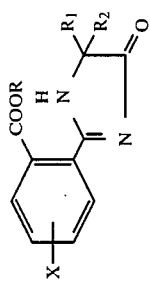

| | | Structure | | Rate kg per | | | | | | | | Plant Species | | | | | | | | |
|---|---|---|---|---|---|---|---|---|---|---|---|---|---|---|---|---|---|---|---|---|
| R₁ | R₂ | R₃ | X | Hectare | PN | SE | MU | PI | RW | MG | TW | VL | BA | CR | FO | WO | CN | CO | SY | RI |
| CH₃ | CH(CH₃)₂ | CH(CH₃)₂<br>—C—CH=CH₂<br>CH(CH₃)₂ | H | 11.2<br>2.24<br>1.12 | 2<br>3<br>0 | 7 | 9 | 9 | 6<br>1<br>0 | 7<br>5<br>5 | 7<br>2<br>0 | 8<br>2<br>0 | 7<br>5<br>0 | 2<br>0<br>0 | 7<br>0<br>0 | 7<br>2<br>0 | 9<br>9 | 5<br>5 | 7<br>7 | |
| CH₃ | CH(CH₃)₂<br>(+) isomer | —C₂H₅ | H | 11.2<br>2.24<br>1.12<br>0.56<br>0.28 | 2<br>7<br>6<br>5<br>3 | 3 | 9 | 9 | 6<br>3<br>2<br>2<br>2 | 7<br>6<br>6<br>6<br>5 | 8<br>8<br>7<br>5<br>3 | 9<br>9<br>9<br>9<br>9 | 6<br>0<br>0<br>0<br>0 | 0<br>0<br>0<br>0<br>0 | 7<br>2<br>0<br>0<br>0 | 9<br>9<br>9<br>3<br>0 | 9<br>9<br>9<br>8 | 7<br>8<br>8<br>6 | 8<br>8<br>8<br>7 | |
| CH₃ | CH(CH₃)₂<br>(−) isomer | —CH₂—C≡CH | H | 11.2<br>2.24<br>1.12<br>0.56<br>0.28<br>0.14<br>0.07 | 3<br>8<br>8<br>7<br>7<br>5 | 9 | 9 | 9 | 9<br>9<br>8<br>7<br>7<br>2 | 9<br>9<br>9<br>9<br>8<br>5 | 9<br>9<br>7<br>5<br>2<br>2 | 9<br>9<br>9<br>9<br>9 | 0<br>7<br>8<br>8<br>6<br>5<br>3 | 0<br>9<br>7<br>7<br>2<br>2<br>0 | 9<br>9<br>9<br>5<br>5<br>2 | 9<br>9<br>9<br>9<br>9 | 9<br>9<br>9<br>9<br>9 | 9<br>9<br>9<br>8<br>8 | 9<br>9<br>9<br>8<br>8<br>8 | |
| CH₃ | CH(CH₃)₂<br>(+) isomer | —CH₂—C—CH₂<br>\|<br>Cl | H | 11.2<br>2.24<br>1.12<br>0.56<br>0.28<br>0.14 | 2<br>7<br>7<br>6<br>6<br>5 | 9 | 9 | 9 | 9<br>8<br>8<br>8<br>3<br>0 | 9<br>9<br>9<br>9<br>8<br>8 | 9<br>9<br>9<br>6<br>5<br>3 | 9<br>9<br>9<br>9<br>9<br>5 | 9<br>7<br>6<br>5<br>3<br>2 | 9<br>3<br>0<br>0<br>0<br>0 | 9<br>9<br>9<br>7<br>5<br>2 | 9<br>9<br>9<br>9<br>9<br>3 | 9<br>9<br>9<br>9<br>8 | 9<br>9<br>9<br>8<br>8 | 9<br>9<br>9<br>8<br>7 | |
| CH₃ | CH(CH₃)₂ | —CH(CH₃)CH=CHCH₃ | 4(5)CH₃ | 11.2<br>2.24<br>1.12<br>0.56<br>0.28 | 2<br>6<br>5<br>3<br>2 | 8 | 9 | 9 | 7<br>7<br>6<br>5<br>2 | 6<br>3<br>2<br>0<br>0 | 8<br>7<br>5<br>3<br>2 | 9<br>8<br>6<br>3<br>0 | 8<br>0<br>0<br>0<br>0 | 7<br>0<br>0<br>0<br>0 | 8<br>3<br>8<br>0<br>0 | 7<br>9<br>9<br>9<br>2 | 9<br>5<br>7<br>3 | 6<br>7<br>2<br>3 | 8 | |
| CH₃<br>CH₃ | CH(CH₃)₂<br>CH(CH₃)₂ | —CH₃<br>—CH₂—C≡CH | 3(6)Cl<br>3(6)Cl | 11.2<br>11.2<br>2.24<br>1.12<br>0.56<br>0.28 | 1<br>0<br>0<br>0<br>0<br>0 | 0<br>0 | 8<br>9 | 9<br>9 | 9<br>7<br>6<br>0<br>0<br>3 | 7<br>6<br>5<br>5<br>9<br>8 | 6<br>5<br>8<br>3<br>2<br>3 | 5<br>5<br>9<br>3<br>0<br>0 | 0<br>0<br>9<br>0<br>0<br>0 | 0<br>0<br>9<br>0<br>0<br>0 | 0<br>0<br>9<br>2<br>0<br>0 | 0<br>0<br>9<br>9<br>5<br>5 | 3<br>0 | 6<br>6 | 2<br>0 | |
| CH₃ | CH(CH₃)₂ | —CH₂—C≡C—CH₂CH | H | 11.2<br>2.24<br>1.12<br>0.56<br>0.28 | 3<br>8<br>7<br>7<br>6 | 8 | 9 | 9 | 9<br>8<br>6<br>3<br>3 | 9<br>9<br>9<br>8<br>8 | 9<br>9<br>6<br>6<br>6 | 9<br>9<br>9<br>9<br>9 | 9<br>9<br>6<br>2<br>2 | 9<br>6<br>8<br>2<br>0 | 9<br>9<br>7<br>6<br>3 | 9<br>9<br>5<br>5 | 9<br>9<br>9 | 8<br>8<br>8<br>8 | 8<br>8<br>8<br>8 | |

TABLE I-continued

Postemergence Herbicidal Activity for Compounds having the Structure:

Structure: benzene ring with X substituent, COOR, N=N-C(R₁)(R₂)-C(=O)- group

| R₁ | R₂ | R₃ | X | Rate kg per Hectare | PN | SE | MU | PI | RW | MG | TW | VL | BA | CR | FO | WO | CN | CO | SY | RI |
|---|---|---|---|---|---|---|---|---|---|---|---|---|---|---|---|---|---|---|---|---|
| CH₃ | CH(CH₃)₂ | —CH₂—C(Cl)—CH₂ | 3(6)Cl | 11.2 | 0 | 0 | 7 | 8 | 0 | 0 | 5 | 5 | 0 | 0 | 0 | 0 | | | | |
| CH₃ | CH(CH₃)₂ | —CH(CH₃)CH=CH—CH₃ | 3(6)Cl | 11.2 | | | | | | | | | | | | | | | | |
| CH₃ | CH(CH₃)₂ | —C₂H₅ | 3(6)NO₂ | 11.2 | 0 | 0 | 6 | 7 | 0 | 0 | 0 | 3 | 0 | 0 | 0 | 0 | 0 | 3 | 0 | |
| | | | | 2.24 | 0 | 0 | 7 | 9 | 5 | 4 | 6 | 5 | 3 | 7 | 1 | 0 | 0 | 2 | 0 | |
| | | | | 1.12 | 0 | 0 | | | 0 | 0 | 3 | 0 | 3 | 0 | 0 | 2 | 0 | 0 | | |
| CH₃ | C₂H₅ | CH₃ | H | 11.2 | 0 | 0 | | | 0 | 0 | 0 | 0 | 0 | 0 | 0 | 0 | 0 | 0 | | |
| CH₃ | C₂H₅ | —CH₂—C≡CH | H | 11.2 | 3 | 0 | 9 | 9 | 0 | 6 | 7 | 9 | 3 | 3 | 7 | 7 | 3 | 3 | 7 | |
| | | | | 2.24 | 3 | | | | 0 | 6 | 8 | 9 | 0 | 0 | 0 | 2 | 0 | 3 | 7 | |
| | | | | 1.12 | 2 | | | | 0 | 7 | 8 | 9 | 3 | 7 | 0 | 3 | 0 | 2 | | |
| CH₃ | C₂H₅ | —CH₂—C(Cl)—CH₂ | H | 11.2 | 3 | 6 | 9 | 9 | 7 | 6 | 8 | 9 | 7 | 7 | 9 | 9 | 9 | 7 | 8 | |
| | | | | 2.24 | 5 | | | | 3 | 7 | 8 | 9 | 8 | 0 | 7 | 9 | 8 | 6 | 8 | |
| | | | | 1.12 | 5 | | | | 2 | 7 | 7 | 9 | 6 | 0 | 7 | 7 | 8 | 5 | 7 | |
| | | | | 0.56 | 3 | | | | 2 | 5 | 7 | 9 | 5 | 0 | 7 | 2 | 8 | 5 | 7 | |
| | | | | 0.28 | 2 | | | | 0 | 3 | 6 | 8 | 0 | 0 | 3 | 0 | 7 | 5 | 7 | |
| CH₃ | C₂H₅ | —CH₂—C(Cl)—CH₂ | H | 11.2 | 5 | 7 | 9 | 9 | 4 | 4 | 7 | 9 | 7 | 5 | 8 | 7 | 9 | 8 | 8 | |
| | | | | 2.24 | 3 | | | | 0 | 8 | 5 | 7 | 7 | 0 | 6 | 6 | 8 | 7 | 7 | |
| | | | | 1.12 | 2 | | | | 0 | 7 | 5 | 6 | 5 | 0 | 2 | 0 | 7 | 6 | 7 | |
| | | | | 0.56 | 1 | | | | 0 | 7 | 0 | 2 | 3 | 0 | 2 | 0 | 7 | 5 | 6 | |
| | | | | 0.28 | 0 | | | | 0 | 7 | 0 | 0 | 0 | 0 | 0 | 0 | 7 | 5 | 6 | |
| CH₃ | CH(CH₃)₂ | —CH₂—C(Cl)—CHCl | H | 11.2 | 3 | 8 | 9 | 9 | 9 | 7 | 8 | 9 | 7 | 8 | 8 | 8 | 9 | 9 | 9 | |
| | | | | 2.24 | 8 | | | | 9 | 9 | 9 | 9 | 8 | 8 | 9 | 9 | 9 | 9 | 9 | |
| | | | | 1.12 | 8 | | | | 8 | 9 | 9 | 8 | 8 | 2 | 8 | 9 | 9 | 9 | 9 | |
| | | | | 0.56 | 8 | | | | 8 | 9 | 7 | 9 | 5 | 0 | 7 | 9 | 9 | 9 | 9 | |
| | | | | 0.28 | 8 | | | | 0 | 9 | 5 | 9 | 5 | 0 | 5 | 5 | 8 | 8 | 9 | |
| CH₃ | C₂H₅ | —CH(CH₃)CH=CHCH₃ | H | 11.2 | 2 | 2 | 9 | 8 | 5 | 7 | 7 | 8 | 7 | 5 | 6 | 7 | 8 | 7 | 7 | |
| | | | | 2.24 | 3 | | | | 0 | 8 | 5 | 7 | 5 | 0 | 2 | 0 | 7 | 6 | 5 | |
| | | | | 1.12 | 3 | | | | 0 | 6 | 2 | 5 | 5 | 0 | 0 | 0 | 7 | 7 | 3 | |
| | | | | 0.56 | 1 | | | | 0 | 5 | 1 | 5 | 3 | 0 | 0 | 0 | 7 | 7 | | |
| CH₃ | CH(CH₃)₂ | —CH₂—C(Cl)—CH₂ | 3(6)NO₂ | 11.2 | 0 | 0 | 9 | 9 | 3 | 3 | 7 | 4 | 2 | 0 | 0 | 0 | 0 | 7 | 0 | |
| | | | | 2.24 | 0 | | | | 2 | 5 | 2 | 2 | 3 | 0 | 0 | 0 | 0 | 3 | 0 | |
| | | | | 1.12 | 0 | | | | 2 | 0 | 0 | 0 | 0 | 0 | 0 | 0 | 0 | | | |

TABLE I-continued

Postemergence Herbicidal Activity for Compounds having the Structure:

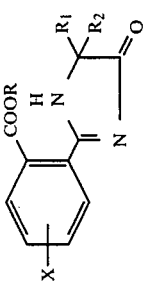

| R₁ | R₂ | R₃ | X | Rate kg per Hectare | PN | SE | MU | PI | RW | MG | TW | VL | BA | CR | FO | WO | CN | CO | SY | RI |
|---|---|---|---|---|---|---|---|---|---|---|---|---|---|---|---|---|---|---|---|---|
| CH₃ | CH(CH₃)₂ | CH₃ / —C—CH—CH₂ / CH₃ | H | 11.2 | 5 | 8 | 9 | 9 | 9 | 7 | 89 | 9 | 7 | 9 | 8 | 9 | 9 | 9 | 9 | |
| | | | | 2.24 | 9 | 9 | 9 | | 9 | 9 | 9 | 9 | 9 | 9 | 9 | 9 | 9 | 9 | 9 | |
| | | | | 1.12 | 9 | 9 | 9 | | 8 | 9 | 9 | 9 | 9 | 3 | 8 | 9 | 9 | 9 | 9 | |
| | | | | 0.56 | 8 | 9 | 9 | | 2 | 9 | 5 | 9 | 7 | 0 | 5 | 5 | 9 | 7 | 8 | |
| | | | | 0.28 | 3 | 3 | 5 | | 0 | 9 | 5 | 5 | 5 | 0 | 0 | 3 | 8 | 3 | 7 | |
| | | | | 0.14 | 3 | | | | 0 | 0 | 0 | 3 | 0 | 0 | 0 | 0 | 7 | 5 | 5 | |
| CH₃ | C₂H₅ | CH₃ / —C—CH—CH₂ / CH₃ | | 11.2 | 4 | 4 | 8 | 8 | 2 | 4 | 4 | 9 | 9 | 4 | 4 | 4 | 9 | 7 | 9 | |
| | | | | 2.24 | 9 | | | | 0 | 9 | 7 | 9 | 9 | 3 | 9 | 7 | 9 | 7 | 9 | |
| | | | | 1.12 | 9 | | | | 0 | 9 | 7 | 9 | 9 | 2 | 8 | 7 | 9 | 7 | 8 | |
| | | | | 0.56 | 8 | | | | 0 | 8 | 3 | 9 | 7 | 0 | 7 | 3 | 7 | 3 | 8 | |
| | | | | 0.28 | 2 | | | | 0 | 6 | 3 | 9 | 3 | 0 | 5 | 3 | 6 | 3 | 7 | |
| | | | | 0.14 | 2 | | | | 0 | 0 | 1 | 3 | 0 | 0 | 3 | 0 | 0 | 2 | 7 | |
| CH₃ | CH(CH₃)₂ | H | 4(5)Cl | 11.2 | 1 | 3 | 6 | 8 | 5 | 4 | 4 | 9 | 4 | 4 | 4 | 4 | 9 | 9 | 9 | |
| | | | | 2.24 | 9 | | | | 9 | 8 | 8 | 9 | 8 | 9 | 9 | 9 | 9 | 9 | 9 | |
| | | | | 1.12 | 5 | | | | 8 | 9 | 8 | 9 | 9 | 9 | 9 | 9 | 9 | 9 | 9 | |
| | | | | 0.56 | 5 | | | | 8 | 8 | 9 | 9 | 7 | 8 | 9 | 8 | 9 | 6 | 9 | |
| | | | | 0.28 | 5 | | | | 6 | 6 | 7 | 9 | 6 | 6 | 8 | 8 | 6 | 9 | 9 | |
| | | | | 0.14 | 0 | | | | 6 | 5 | 8 | 8 | 5 | 5 | 6 | 9 | 3 | 9 | 5 | |
| CH₃ | CH(CH₃)₂ | CH(CH₃)₂ / —C—C≡CH / CH(CH₃)₂ | H | 11.2 | 0 | 6 | 9 | 9 | 3 | 0 | 7 | 7 | 4 | 7 | 4 | 7 | 9 | 9 | 9 | |
| | | | | 2.24 | 6 | | | | 2 | 9 | 8 | 9 | 7 | 7 | 3 | 8 | 9 | 9 | 9 | |
| | | | | 1.12 | 5 | | | | 1 | 9 | 7 | 9 | 5 | 5 | 3 | 9 | 8 | 9 | 9 | |
| | | | | 0.56 | 5 | | | | 0 | 9 | 6 | 8 | 3 | 3 | 1 | 3 | 3 | 7 | 5 | |
| | | | | 0.28 | 3 | | | | 0 | 9 | 5 | 7 | 3 | 0 | | | | | | |
| CH₃ | CH(CH₃)₂ | —C₂H₅ | 4(5)Cl | 11.2 | 0 | 0 | 9 | 9 | 7 | 2 | 7 | 7 | 4 | 1 | 2 | 7 | 0 | 0 | 5 | |
| | | | | 2.24 | 0 | | | | 6 | 7 | 5 | 5 | 0 | 0 | 0 | 2 | 0 | 7 | 3 | |
| | | | | 1.12 | 0 | | | | 1 | 6 | 1 | 3 | 0 | 0 | 0 | 0 | | 3 | | |
| C₂H₅ | CH(CH₃)₂ | CH₃ | H | 11.2 | 0 | 0 | 6 | 8 | 0 | 0 | 5 | 5 | 0 | 0 | 0 | 0 | | | | |
| C₂H₅ | CH(CH₃)₂ | —CH₂—C≡CH | H | 11.2 | 0 | 6 | 8 | 8 | 0 | 2 | 5 | 7 | 0 | 0 | 0 | 0 | | | | |
| C₂H₅ | CH(CH₃)₂ | —CH₂—C—CH₂ / Cl | H | 11.2 | 0 | 0 | 8 | 8 | 0 | 1 | 7 | 7 | 0 | 0 | 0 | 0 | | | | |
| CH₃ | CH(CH₃)₂ | —CH₂—O≡CH | 4(5)Cl | 11.2 | 0 | 0 | 7 | 8 | 3 | 0 | 5 | 5 | 4 | 1 | 4 | 4 | | | | |
| CH₃ | CH(CH₃)₂ | —CH(CH₃)CH=CHCH₃ | 4(5)Cl | 11.2 | 2 | 6 | 8 | 8 | 4 | 4 | 7 | 9 | 7 | 4 | 4 | 4 | | | | |

TABLE I-continued

Postemergence Herbicidal Activity for Compounds having the Structure:

(benzene ring with X substituent, COOR group, and —N=C(—NH—)—C(R1)(R2)—C(=O)— side chain)

| R1 | R2 | R3 | X | Rate kg per Hectare | PN | SE | MU | PI | RW | MG | TW | VL | BA | CR | FO | WO | CN | CO | SY | RI |
|---|---|---|---|---|---|---|---|---|---|---|---|---|---|---|---|---|---|---|---|---|
| CH3 | C2H5 | H | H | 2.24 | 3 | | | | 2 | 9 | 5 | 8 | 5 | 0 | 2 | 7 | 6 | 6 | 7 | |
| | | | | 1.12 | 3 | | | | 2 | 6 | 6 | 6 | 5 | 0 | 2 | 2 | 5 | 5 | 7 | |
| | | | | 0.56 | 3 | | | | 2 | 6 | 5 | 5 | 5 | 0 | 2 | 2 | 0 | 5 | 5 | |
| C2H5 | CH(CH3)2 | H | H | 11.2 | 3 | 8 | 8 | 8 | 0 | 6 | 7 | 9 | 7 | 4 | 7 | 7 | | | | |
| | | | | 2.24 | 2 | 5 | 7 | 8 | 1 | 8 | 7 | 8 | 6 | 2 | 4 | 4 | | | | |
| | | | | 1.12 | 3 | | | | 2 | 9 | 8 | 9 | 7 | 7 | 7 | 9 | 8 | 8 | 8 | |
| | | | | 0.56 | 3 | | | | 2 | 9 | 8 | 9 | 7 | 5 | 7 | 8 | 9 | 8 | 6 | |
| CH3 | CH(CH3)2 | H | 3(6)Cl | 11.2 | 3 | 7 | 7 | 9 | 0 | 9 | 3 | 9 | 6 | 0 | 5 | 6 | 8 | 7 | 5 | |
| CH3 | CH(CH3)2 | —CH2—C(Cl)—CH2 | 4(5)Cl | 11.2 | 2 | 7 | 8 | 9 | 7 | 7 | 7 | 8 | 6 | 5 | 7 | 5 | | | | |
| CH3 | CH(CH3)2 | CH=CH2 / —CH—C≡CH | H | 11.2 | 7 | 8 | 8 | 9 | 6 | 8 | 7 | 9 | 7 | 8 | 8 | 7 | | | | |
| CH3 | CH(CH3)2 | —C(CH3)(CH3)—CH=CH2 | 4(5)Cl | 11.2 | 4 | 7 | 8 | 7 | 6 | 6 | 6 | 9 | 7 | 3 | 7 | 9 | | | | |

* = Average of two or more tests

EXAMPLE 7

Preemergence Herbicidal Activity

The preemergence herbicidal activity of the compounds of the present invention is exemplified by the following tests in which the seeds or propagating organs of a variety of monocotyledonous, cyperaceous and dicotyledonous plants are separately mixed with potting soil and planted on top of approximately 2.5 cu of soil in separate (size) cups. After planting, the cups are sprayed with the selected aqueous acetone solution containing test compound in sufficient quantity to provide the equivalent of about 0.28 kg to 11.2 kg per hectare of test compound per cup. The treated cups are then placed on greenhouse benches, watered and cared for in accordance with conventional greenhouse procedures. Three or four weeks after treatment, the tests are terminated and each cup is examined and rated according to the rating system set forth in Example 6. The herbicidal proficiency of the active ingredients of the present invention is evident from the test results which are reported in Table II below.

TABLE II
Preemergence Herbicidal Activity for Compounds having the Structure:
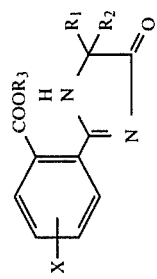
| R₁ | R₂ | R₃ Structure | X | Rate kg per Hectare | PN | SE | MU | PI | RW | MO | TW | VL | BA | CR | FO | WO | CN | CO | SY | RI | JW |
|---|---|---|---|---|---|---|---|---|---|---|---|---|---|---|---|---|---|---|---|---|---|
| CH₃ | —CH(CH₃)₂ | —CH₂C≡CH | H | 11.2 | 9 | 8 | 8 | 9 | 9 | 9 | 8 | 9 | 9 | 9 | 9 | 8 | — | — | — | — | — |
|  |  |  |  | 4.48 | 9 | 9 | 9 | 9 | 9 | 9 | 8 | 8 | 9 | 9 | 9 | 9 | 9 | 9 | 9 | 9 | — |
|  |  |  |  | 1.12* | 9 | 7.5 | 9 | 9 | 5 | 8 | 8.5 | 8.5 | 9 | 9 | 9 | 8.5 | 8.5 | 9 | 8 | 9 | — |
|  |  |  |  | 0.56* | 9 | 6.5 | 9 | 9 | 3 | 7 | 7.5 | 8.5 | 7.5 | 7 | 9 | 7 | 7.5 | 8 | 8 | 8.5 | — |
|  |  |  |  | 0.28 | 8 | 0 | 8 | 9 | 0 | 5 | 5 | 6 | 6 | — | 6 | 7 | 9 | 8 | 7 | 6 | — |
|  |  |  |  | 0.07 | 8 | 0 | 9 | 9 | 3 | 5 | 5 | 6 | 5 | 7 | 7 | 7 | 5 | — | 7 | — | — |
| CH₃ | —CH(CH₃)₂ | —CH₂CH₂CH₃ | H | 11.2 | 9 | 8 | 9 | 9 | 9 | 8 | 8 | 8 | 8 | 8 | 9 | 8 | — | — | — | — | — |
|  |  |  |  | 4.48 | 6 | 8 | 8 | 9 | 2 | 8 | 8 | 8 | 7 | 8 | 9 | 8 | 7 | 9 | 8 | 6 | — |
|  |  |  |  | 1.12 | 3 | 7 | 7 | 9 | 0 | 7 | 7 | 2 | 6 | 7 | 8 | 7 | 3 | 8 | 5 | 0 | — |
|  |  |  |  | 0.56 | 2 | 7 | 7 | 9 | 0 | 4 | 5 | 1 | 0 | 0 | 0 | 4 | 1 | 7 | 1 | 0 | — |
| CH₃ | —CH(CH₃)₂ |  | H | 11.2 | 9 | 8 | 9 | 9 | 8 | 8 | 9 | 9 | 9 | 9 | 9 | 8 | — | — | — | — | — |
|  |  |  |  | 4.48 | 9 | 8 | 9 | 9 | 5 | 8 | 9 | 8 | 8 | 8 | 9 | 7 | 3 | 9 | 8 | 9 | — |
|  |  |  |  | 1.12 | 8 | 5 | 8 | 9 | 0 | 7 | 7 | 7 | 5 | 7 | 7 | 7 | 2 | 7 | 3 | 7 | — |
|  |  |  |  | 0.56 | 1 | 0 | 8 | 9 | 0 | 7 | 5 | 5 | 0 | 2 | 3 | 0 | 1 | 1 | 0 | 3 | — |
| CH₃ | —CH(CH₃)₂ | —(CH₂)₇CH₃ | H | 11.2 | 9 | 3 | 9 | 9 | 8 | 7 | 8 | 7 | 9 | 9 | 9 | 4 | — | — | — | — | — |
|  |  |  |  | 4.48 | 9 | 9 | 8 | 9 | 0 | 7 | 7 | 6 | 7 | 8 | 9 | 5 | 5 | 6 | 6 | 8 | — |
|  |  |  |  | 1.12 | 9 | 0 | 9 | 9 | — | 7 | 2 | 3 | 5 | 5 | 8 | 2 | 2 | 2 | 3 | 7 | — |
|  |  |  |  | 0.56 | 8 | 0 | 8 | 9 | 0 | 7 | 0 | 2 | 0 | 2 | 7 | 0 | 2 | 0 | 3 | 3 | — |
| CH₃ | —CH(CH₃)₂ | —(CH₂)₁₁CH₃ | H | 11.2 | 9 | 3 | 9 | 9 | 0 | 7 | 7 | 7 | 8 | 7 | 9 | 4 | — | — | — | — | — |
|  |  |  |  | 4.48 | 9 | 5 | 8 | 9 | 0 | 7 | 7 | 8 | 7 | 8 | 9 | 4 | 7 | 6 | 7 | 8 | — |
|  |  |  |  | 1.12 | 9 | 0 | 8 | 9 | 0 | 6 | 6 | 7 | 3 | 6 | 8 | 2 | 2 | 2 | 2 | 7 | — |
|  |  |  |  | 0.56 | 6 | 3 | 7 | 9 | 0 | 2 | 3 | 6 | 3 | 2 | 7 | 0 | 2 | 0 | 1 | 2 | — |
| CH₃ | —CH(CH₃)₂ | —CH₂CH=CH₂ | H | 11.2 | 9 | 0 | 9 | 9 | 8 | 8 | 9 | 9 | 8 | 9 | 9 | 8 | — | — | — | — | — |
|  |  |  |  | 4.48 | 9 | 8 | 8 | 9 | 8 | 8 | 8 | 9 | 8 | 9 | 9 | 8 | 8 | 9 | 9 | 9 | — |
|  |  |  |  | 1.12 | 9 | 7 | 8 | 9 | 5 | 7 | 7 | 7 | 7 | 7 | 8 | 7 | 8 | 8 | 8 | 7 | — |
|  |  |  |  | 0.56 | 9 | 0 | 8 | 9 | 0 | 2 | 2 | 6 | 5 | 5 | 7 | 7 | 7 | 8 | 7 | 2 | — |
| CH₃ | —CH(CH₃)₂ | —CH₃ | H | 11.2 | 9 | 9 | 9 | 9 | 7 | 8 | 9 | 9 | 9 | 9 | 9 | 9 | 9 | 9 | 9 | 9 | — |
|  |  |  |  | 4.48 | 9 | 9 | 9 | 9 | 2 | 9 | 9 | 9 | 9 | 8 | 9 | 9 | 9 | 9 | 9 | 8 | — |
|  |  |  |  | 1.12* | 7.6 | 3.5 | 9 | 9 | 0 | 7.6 | 5 | 8 | 7.5 | 4.5 | 7 | 8.6 | 7 | 7.6 | 7.6 | 6.5 | — |
|  |  |  |  | 0.56* | 5.6 | 0 | 9 | 9 | 0 | 7.3 | 3.5 | 6.7 | 5.5 | 1 | 5 | 8.3 | 4 | 7.3 | 6.7 | 1.5 | — |
|  |  |  |  | 0.28 | 3 | 0 | 8 | 8 | 0 | 7 | 0 | 1 | 2 | 0 | 2 | 8 | 0 | 7 | 3 | 1 | — |
| CH₃ | —CH(CH₃)₂ | —C(CH₃)₂CH=CH₂ | H | 11.2 | 9 | 8 | 9 | 9 | 8 | 8 | 8 | 9 | 9 | 9 | 9 | 8 | 9 | 9 | 9 | 9 | — |
|  |  |  |  | 4.48 | 9 | 9 | 9 | 9 | 8 | 9 | 9 | 9 | 9 | 9 | 9 | 8 | 9 | 8 | 9 | 9 | — |
|  |  |  |  | 1.12 | 9 | 8 | 9 | 9 | 5 | 5 | 7 | 8 | 7 | 8 | 8 | 7 | — | 7 | 8 | 5 | — |
|  |  |  |  | 0.56 | 9 | 6 | 8 | 8 | 0 | 7 | 2 | 5 | 0 | 2 | 6 | 6 | — | — | 1 | — | — |
|  |  |  |  | 0.07 | 9 | 0 | 8 | 9 | 8 | 8 | 8 | 8 | 8 | 9 | 9 | 0 | 9 | — | — | — | — |
| CH₃ | —CH(CH₃)₂ | —C(CH₃)₂C≡CH | H | 11.2 | 9 | 8 | 8 | 9 | 8 | 8 | 8 | 8 | 8 | 9 | 9 | 8 | — | — | — | — | — |

TABLE II-continued

Preemergence Herbicidal Activity for Compounds having the Structure:

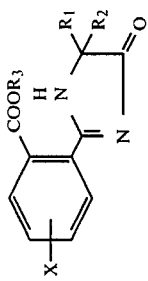

| R₁ | R₂ | Structure R₃ | X | Rate kg per Hectare | PN | SE | MU | PI | RW | MO | TW | VL | BA | CR | FO | WO | CN | CO | SY | RI | JW |
|---|---|---|---|---|---|---|---|---|---|---|---|---|---|---|---|---|---|---|---|---|---|
| CH₃ | —CH(CH₃)₂ | —CH(CH₃)₂ | H | 0.56 | 8 | 0 | 8 | 9 | 0 | 8 | 5 | 6 | 6 | 6 | 7 | 7 | 5 | 8 | 5 | 0 | — |
| CH₃ | —CH(CH₃)₂ | —C(CH₃)₃ | H | 11.2 | 7 | 5 | 8 | 9 | 3 | 8 | 8 | 8 | 7 | 9 | 9 | 8 | — | — | — | — | — |
| | | | | 11.2 | 9 | 5 | 8 | 9 | 7 | 0 | 0 | 0 | 6 | 7 | 8 | 7 | 0 | 8 | 0 | — | — |
| CH₃ | —CH(CH₃)₂ | —CH₂CH₃ | H | 0.06 | 0 | 0 | 2 | 9 | 0 | 8 | 0 | 0 | 0 | 0 | 0 | 7 | 0 | — | — | — | — |
| | | | | 11.2 | 9 | 8 | 8 | 9 | 7 | 8 | 9 | 9 | 7 | 7 | 7 | 9 | 2 | 7 | 1 | — | 8 |
| CH₃ | —CH(CH₃)₂ | —C(CH₃)₂CH=CH₂ | H | 11.2 | 9 | 0 | 8 | 6 | 1 | 6 | 2 | 5 | 0 | 2 | 5 | 1 | — | — | — | — | 7 |
| CH₃ | —CH(CH₃)₂ | —CH(CH₃)C≡CH | H | 11.2 | 9 | 9 | 9 | 9 | 9 | 4 | 6 | 6 | 0 | 0 | 0 | 0 | — | — | — | — | — |
| CH₃ | —CH(CH₃)₂ | —CH₂C(Cl)=CH₂ | H | 0.56 | 9 | 9 | 9 | — | 3 | 8 | 9 | 9 | 9 | 9 | 9 | 8 | — | 9 | 9 | — | 8 |
| | | | | 11.2 | 8 | 9 | 8 | 9 | 8 | 8 | 9 | 7 | 9 | 7 | 8 | 9 | 1 | 2 | 7 | — | 7 |
| CH₃ | —CH(CH₃)₂ | —CH₂C(Cl)=CH₂ | H | 0.14 | 9 | 9 | — | — | 0 | 8 | 9 | 9 | 9 | 7 | 8 | 8 | — | — | 9 | — | 9 |
| CH₃ | —CH(CH₃)₂ | —CH₂CH₂C≡CH | H | 11.2 | 9 | 9 | 9 | 8 | 8 | 8 | 8 | 7 | 7 | 6 | 8 | 8 | 8 | 8 | 8 | — | 9 |
| CH₃ | —CH(CH₃)₂ | —CH(CH₃)CHCH₂ | H | 2.24 | 9 | 9 | 9 | 9 | 2 | 8 | 9 | 9 | 8 | 7 | 8 | 7 | — | — | 5 | — | 8 |
| | | | | 11.2 | 9 | 0 | 9 | 9 | 8 | 8 | 9 | 6 | 6 | 7 | 6 | 7 | 7 | 0 | — | — | — |
| | | —C(CH₃)₂CH=CH₂ | H | 1.12 | 9 | 9 | 9 | — | 0 | 7 | 9 | 9 | 8 | 9 | 8 | 9 | 0 | 0 | 0 | — | 9 |
| | | —CH₂C≡CH | H | 11.2 | 9 | 0 | 9 | 9 | 0 | 9 | 5 | 0 | 9 | 9 | 6 | 0 | 0 | 0 | 0 | — | 0 |
| —(CH₂)₅— | | | | 0.56 | 9 | 9 | 9 | — | 7 | 2 | 0 | 0 | 8 | 9 | 9 | 7 | 8 | 8 | 6 | — | 9 |
| —CH(CH₃)CH₂CH₂CH₂CH₂— | | | | 0.14 | 6 | 0 | — | — | 0 | 0 | 0 | 0 | 6 | 7 | 7 | 0 | 0 | 0 | 0 | — | 0 |
| CH₃ | —CH(CH₃)₂ | —CH(CH₃)—C(CH₃)=CH₂ | H | 11.2 | 0 | 0 | — | — | 8 | 8 | 8 | 9 | 9 | 9 | 9 | 7 | 8 | 8 | 0 | — | 8 |
| | | | | 2.24 | 9 | 9 | — | — | 1 | 8 | 8 | 8 | 8 | 9 | 8 | 7 | — | — | 6 | — | 0 |
| CH₃ | —CH(CH₃)₂ | —CH₂CH=CHCH₃ | H | 11.2 | 9 | 9 | 9 | 9 | 8 | 8 | 8 | 9 | 7 | 6 | 8 | 8 | 8 | 9 | 8 | — | 9 |
| | | | | 2.24 | 9 | 9 | 9 | 8 | 2 | 8 | 8 | 8 | 8 | 7 | 9 | 8 | 8 | 8 | 8 | — | 9 |
| CH₃ | —CH(CH₃)₂ | —CH₂C(CH₃)=CH₂ | H | 11.2 | 9 | 9 | 9 | 9 | 0 | 8 | 9 | 9 | 7 | 7 | 8 | 7 | 3 | — | 3 | — | 9 |
| CH₃ | —CH(CH₃)₂ | —CH₂CH=C(CH₃)₂ | H | 0.56 | 8 | 9 | 8 | 8 | 8 | 8 | 9 | 9 | 6 | 6 | 7 | 2 | — | — | 9 | — | 0 |
| | | | | 0.28 | 9 | 0 | — | — | 0 | 7 | 9 | 8 | 9 | 9 | 9 | 8 | — | 8 | — | — | 9 |
| CH₃ | —CH(CH₃)₂ | | H | 11.2 | 3 | — | — | — | 0 | 7 | 8 | 8 | 7 | 8 | 9 | 0 | — | — | 5 | — | — |
| | | | | 2.28 | 8 | 8 | — | — | 0 | 9 | 9 | 6 | 3 | 5 | 5 | 0 | 1 | 3 | — | — | 9 |
| CH₃ | —CH(CH₃)₂ | —CH(CH=CH₂)₂ | H | 11.2 | 9 | — | — | — | 8 | 9 | 8 | 8 | 9 | 9 | 9 | 8 | — | 8 | 8 | — | 8 |
| | | | | 1.12 | 9 | — | — | — | 0 | 8 | 8 | 8 | 7 | 7 | 9 | 3 | 8 | 8 | 5 | — | 8 |
| | | | | 0.25 | 9 | — | — | — | 0 | 7 | 7 | 6 | 7 | 6 | 7 | 0 | 2 | 0 | 0 | — | 7 |
| | | | | 0.07 | 7 | — | — | — | 2 | 2 | 0 | 0 | 0 | 3 | 2 | 0 | 0 | — | — | — | — |
| CH₃ | —CH(CH₃)₂ | —CH(CH₃)—CH=CHCH₃ | H | 11.2 | 9 | 9 | 8 | 8 | 9 | 9 | 8 | 8 | 9 | 9 | 9 | 8 | — | 8 | 9 | — | 8 |
| | | | | 0.56 | 9 | 0 | — | — | 0 | 7 | 7 | 8 | 7 | 7 | 9 | 6 | — | 8 | 8 | — | 8 |

TABLE II-continued

Preemergence Herbicidal Activity for Compounds having the Structure:

[Structure: substituted benzene ring with X, COOR₃ group, and N=C(R₁)(R₂)-C(=O)- moiety]

| R₁ | R₂ | Structure R₃ | X | Rate kg per Hectare | PN | SE | MU | PI | RW | MO | TW | VL | BA | CR | FO | WO | CN | CO | SY | RI | JW |
|---|---|---|---|---|---|---|---|---|---|---|---|---|---|---|---|---|---|---|---|---|---|
| CH₃ | —CH(CH₃)₂ | —CH₂-(cyclohex-3-enyl) | H | 11.2 | 8 | 8 | 8 | 8 | 0 | 8 | 8 | 8 | 7 | 8 | 8 | 5 | — | — | — | — | — |
|  |  |  |  | 2.24 | 9 | — | — | — | 0 | 7 | 8 | 6 | 6 | 6 | 7 | 2 | 3 | 8 | 9 | — | 8 |
| CH₃ | —CH(CH₃)₂ | —C(CH₃)₂CH=CH₂ HCl salt | H | 11.2 | 9 | 9 | 9 | 9 | 8 | 8 | 8 | 8 | 9 | 9 | 9 | 9 | — | — | — | — | — |
|  |  |  |  | 1.12 | 9 | 6 | 8 | 9 | 8 | 8 | 7 | 8 | 6 | 7 | 9 | 8 | 8 | 9 | 9 | 9 | 7 |
|  |  |  |  | 0.56 | 9 | 0 | 8 | 9 | 0 | 8 | 7 | 7 | 3 | 8 | 9 | 8 | 7 | 8 | 7 | 9 | 7 |
|  |  |  |  | 0.14 | 9 | 0 | 8 | 9 | 6 | 3 | 0 | 5 | 3 | 5 | 7 | 0 | 1 | 6 | 7 | 9 | 7 |
| CH₃ | —CH(CH₃)₂ | —C(CH₃)₂C≡CH HCl salt | H | 11.2 | 9 | 0 | 8 | 9 | 1 | 8 | 9 | 9 | 8 | 9 | 9 | 8 | — | — | — | — | — |
|  |  |  |  | 1.12 | 8 | 0 | 8 | 9 | 0 | 8 | 6 | 7 | 8 | 7 | 8 | 8 | 7 | 7 | 7 | 8 | 7 |
|  |  |  |  | 0.56 | 2 | 0 | 8 | 9 | 0 | 8 | 0 | 0 | 7 | 3 | 7 | 7 | 7 | 8 | 6 | 7 | — |
|  |  |  |  | 0.14 | 8 | 0 | 8 | 9 | 0 | 7 | 0 | 3 | 2 | 2 | 3 | 1 | 3 | 7 | 1 | 1 | — |
| CH₃ | CH(CH₃)₂ | —CH₂C(CH₃)₃ | H | 11.2 | 2 | — | — | — | 3 | 7 | 0 | 1 | 3 | 5 | 2 | 6 | 0 | 7 | 2 | — | 7 |
|  |  |  |  | 2.24 | 0 | — | — | — | 0 | 0 | 9 | 8 | 0 | 0 | 0 | 2 | 0 | 0 | 0 | — | 7 |
|  |  |  |  | 1.12 | 2 | — | — | — | 0 | 7 | 7 | 5 | 0 | 0 | 5 | 2 | 0 | 7 | — | — | — |
| CH₃ | CH(CH₃)₂ | —CH₂CH₂OCH₃ | H | 11.2 | 9 | 7 | 9 | 9 | 3 | 8 | 8 | 8 | 8 | 8 | 9 | 8 | 2 | 6 | 6 | — | 9 |
|  |  |  |  | 2.24 | 5 | — | — | — | 0 | 2 | 7 | 3 | 0 | 0 | 0 | 6 | 1 | 2 | 2 | — | 9 |
|  |  |  |  | 1.12 | 5 | — | — | — | 0 | 0 | 0 | 1 | 0 | 0 | 0 | 2 | — | — | — | — | 7 |
| CH₃ | CH(CH₃)₂ | —CH₂-(furyl) | H | 11.2 | 9 | 8 | 9 | 9 | 8 | 9 | 9 | 9 | 9 | 9 | 9 | 8 | 9 | 8 | 8 | 9 | 9 |
|  |  |  |  | 2.24 | 9 | — | — | — | 8 | 8 | 8 | 8 | 9 | 9 | 9 | 8 | 8 | 8 | 8 | 9 | 9 |
|  |  |  |  | 1.12 | 9 | — | — | — | 8 | 8 | 8 | 8 | 7 | 8 | 9 | 7 | 8 | 7 | 8 | 8 | 8 |
|  |  |  |  | 0.56 | 9 | — | — | — | 2 | 7 | 7 | 8 | 0 | 7 | 9 | 3 | 5 | 5 | 7 | 9 | 9 |
|  |  |  |  | 0.28 | 9 | — | — | — | 0 | 7 | 7 | 7 | 1 | 0 | 9 | 3 | — | — | — | — | — |
| CH₃ | CH(CH₃)₂ | —C₆H₁₃-n | H | 11.2 | 9 | 8 | 9 | 9 | 7 | 8 | 8 | 8 | 8 | 8 | 9 | 7 | 2 | 8 | 6 | 9 | 9 |
|  |  |  |  | 2.24 | 9 | — | — | — | 2 | 2 | 9 | 6 | 2 | 3 | 9 | 2 | 1 | 2 | 2 | 7 | 7 |
|  |  |  |  | 1.12 | 9 | — | — | — | 0 | 0 | 3 | 5 | 0 | 0 | 0 | 1 | — | — | — | — | — |
| CH₃ | CH(CH₃)₂ | —C(CH₃)(C₂H₅)CH₃ (tert-amyl) | H | 11.2 | 9 | 8 | 9 | 9 | 9 | 8 | 9 | 9 | 9 | 9 | 9 | 8 | 3 | 8 | 7 | 9 | 9 |
|  |  |  |  | 2.24 | 9 | — | — | — | 0 | 8 | 9 | 8 | 2 | 3 | 3 | 2 | 2 | 5 | 3 | — | — |
|  |  |  |  | 1.12 | 9 | — | — | — | 0 | 5 | 9 | 3 | 0 | 0 | 0 | 0 | — | — | — | — | — |
| CH₃ | CH(CH₃)₂ | —CH₂CH₂OC₂H₅ | H | 11.2 | 9 | 8 | 8 | 9 | 5 | 8 | 8 | 8 | 8 | 8 | 9 | 8 |  |  |  |  |  |

TABLE II-continued
Preemergence Herbicidal Activity for Compounds having the Structure:
| Structure | | | Rate kg per | Plant Species | | | | | | | | | | | | | | |
|---|---|---|---|---|---|---|---|---|---|---|---|---|---|---|---|---|---|---|
| R1 | R2 | R3 | X | Hectare | PN | SE | MU | PI | RW | MO | TW | VL | BA | CR | FO | WO | CN | CO | SY | RI | JW |
| CH3 | CH(CH3)2 | —CH2CH=CH—C6H5 | H | 2.24 | 9 | | | | 0 | 2 | 1 | 5 | 0 | 0 | 2 | 5 | 6 | 5 | 6 | | 8 |
| | | | | 1.12 | 2 | | | | 0 | 1 | 0 | 3 | 0 | 0 | 0 | 1 | 0 | 0 | 4 | | 6 |
| CH3 | CH(CH3)2 | —CH2—C≡C—C6H5 | H | 2.24 | 9 | 9 | 9 | 9 | 7 | 8 | 9 | 9 | 9 | 9 | 9 | 8 | 6 | 8 | | | 8 |
| | | | | 1.12 | 8 | | | | 0 | 6 | 6 | 7 | 1 | 1 | 9 | 6 | 3 | 8 | 5 | | |
| CH3 | CH(CH3)2 | —CH2—C≡C—C6H5 | H | 2.24 | 9 | 8 | 9 | 9 | 8 | 8 | 8 | 8 | 9 | 9 | 9 | 6 | 0 | 0 | 3 | | 8 |
| | | | | 1.12 | 6 | | | | 0 | 3 | 3 | 6 | 0 | 0 | 9 | 0 | 0 | 0 | | | |
| CH3 | CH(CH3)2 | —CH2—C≡C—CH3 | H | 2.24 | 9 | 8 | 9 | 9 | 8 | 8 | 8 | 9 | 6 | 6 | 9 | 3 | 5 | 2 | 3 | | 8 |
| | | | | 1.12 | 8 | | | | 3 | 3 | 7 | 6 | 6 | 6 | 9 | 5 | 2 | 0 | 0 | | 2 |
| | | | | | 9 | 9 | | | 9 | 0 | 2 | 3 | 2 | 0 | 5 | 2 | 0 | 0 | 0 | | |
| CH3 | CH(CH3)2 | | H | 11.2 | 9 | 9 | 9 | 9 | 9 | 9 | 9 | 9 | 9 | 9 | 9 | 9 | 8 | 8 | 7 | | 9 |
| | | | | 2.24 | 9 | | | | 7 | 8 | 9 | 9 | 6 | 8 | 9 | 8 | 8 | 7 | 7 | | 9 |
| | | | | 1.12 | 9 | | | | 2 | 2 | 9 | 9 | 5 | 3 | 8 | 2 | 8 | 7 | 7 | | 8 |
| | | | | 0.56 | 9 | | | | 0 | 0 | 5 | 7 | 3 | 2 | 0 | 7 | 2 | 7 | 7 | | 8 |
| | | | | 0.28 | 6 | | | | 0 | 5 | 7 | 3 | 2 | 0 | 7 | 0 | 3 | 7 | 5 | | 7 |
| CH3 | CH(CH3)2 | 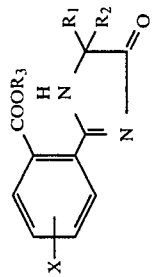 —CH—CH3 | H | 11.2 | 9 | 8 | 9 | 9 | 9 | 8 | 9 | 9 | 9 | 9 | 9 | 9 | 9 | 8 | 8 | | 8 |
| | | | | 2.24 | 9 | | | | 5 | 8 | 8 | 9 | 9 | 7 | 7 | 8 | 7 | 7 | 6 | | 8 |
| | | | | 1.12 | 9 | | | | 0 | 6 | 7 | 7 | 7 | 0 | 7 | 3 | 7 | 7 | 5 | | 2 |
| | | | | 0.56 | 9 | | | | 0 | 3 | 5 | 2 | 0 | 0 | 0 | 0 | 1 | 7 | | | |
| CH3 | CH(CH3)2 | —CH2—C≡C—C7H15—n | H | 11.2 | 9 | 1 | 8 | 9 | 3 | 8 | 8 | 8 | 8 | 9 | 9 | 7 | 5 | 5 | 6 | | 7 |
| | | | | 2.24 | 9 | | | | 0 | 6 | 6 | 9 | 9 | 2 | 0 | 8 | 9 | 2 | 5 | | 7 |
| | | | | 1.12 | 9 | | | | 0 | 3 | 3 | 2 | 7 | 0 | 7 | 8 | 5 | 2 | 2 | | 7 |
| | | | | 0.56 | 0 | | | | 0 | 2 | 0 | 3 | 0 | 0 | 0 | 0 | 2 | 1 | 3 | | 3 |
| CH3 | CH(CH3)2 | —CH2CCl3 | H | 11.2 | 9 | 8 | 9 | 9 | 8 | 8 | 8 | 9 | 8 | 8 | 9 | 8 | 8 | 8 | 8 | | 8 |
| | | | | 2.24 | 9 | | | | 7 | 8 | 6 | 9 | 8 | 6 | 9 | 8 | 8 | 7 | 8 | | 7 |
| | | | | 1.12 | 9 | | | | 3 | 8 | 5 | 9 | 5 | 2 | 8 | 7 | 7 | 7 | 7 | | 6 |
| | | | | 0.56 | 9 | | | | 0 | 2 | 5 | 7 | 3 | 0 | 7 | 7 | 3 | 7 | 6 | | 3 |
| | | | | 0.28 | 9 | | | | 0 | 6 | 9 | 2 | 3 | 0 | 5 | 5 | 3 | 7 | | | |
| CH3 | CH(CH3)2 | —C(C2H5)2CH=CH2 | H | 11.2 | 9 | 9 | 8 | 9 | 8 | 9 | 9 | 9 | 9 | 8 | 9 | 9 | 9 | 8 | 8 | | 9 |
| | | | | 2.24 | 9 | | | | 5 | 8 | 9 | 9 | 7 | 3 | 7 | 9 | 8 | 7 | 7 | | 8 |
| | | | | 1.12 | 9 | | | | 3 | 8 | 5 | 7 | 5 | 0 | 7 | 5 | 7 | 7 | 7 | | 6 |
| | | | | 0.56 | 9 | | | | 0 | 7 | 0 | 6 | 0 | 0 | 3 | 5 | 7 | 7 | 7 | | 3 |

TABLE II-continued

Preemergence Herbicidal Activity for Compounds having the Structure:

(benzene ring with COOR₃, NH, and C(R₁)(R₂)C(=O)N substituents; X on ring)

| R₁ | R₂ | R₃ (Structure) | X | Rate kg per Hectare | PN | SE | MU | PI | RW | MO | TW | VL | BA | CR | FO | WO | CN | CO | SY | RI | JW |
|---|---|---|---|---|---|---|---|---|---|---|---|---|---|---|---|---|---|---|---|---|---|
| CH₃ | CH(CH₃)₂ | CH(CH₃)₂ / cyclohexane(CH₃)(CH₃) | H | 11.2 | 0 | 0 | 0 | 8 | 0 | 4 | 0 | 0 | 0 | 0 | 3 | 0 | | | | | |
| CH₃ | CH(CH₃)₂ | cyclohexane(CH₃)(C≡CH) | H | 11.2 | 0 | 0 | 8 | 9 | 0 | 7 | 6 | 7 | 3 | 5 | 6 | 3 | | | | | |
| CH₃ | CH(CH₃)₂ | —CH₂—C(Cl)=CH₂ | 4(5)CH₃ | 11.2 | 9 | 7 | 9 | 9 | 8 | 8 | 8 | 8 | 9 | 9 | 9 | 8 | 6 | 7 | 7 | | 8 |
| | | | | 2.24 | 9 | | 8 | 7 | 8 | 8 | 8 | 8 | 8 | 8 | 9 | 9 | 1 | 5 | 6 | | 8 |
| | | | | 1.12 | 7 | | 8 | 2 | 7 | 5 | 7 | 7 | 8 | 5 | 8 | 9 | 0 | 3 | 3 | | 7 |
| | | | | 0.56 | 5 | | 9 | 0 | 5 | 2 | 7 | 5 | 0 | 0 | 0 | 8 | | | | | |
| CH₃ | CH(CH₃)₂ | —CH₃ | 4(5)CH₃ | 11.2 | 9 | 8 | 9 | 9 | 8 | 7 | 8 | 9 | 9 | 8 | 8 | 8 | 8 | 5 | 7 | | 7 |
| | | | | 2.24 | 8* | | 8 | 7 | 4* | 7.5 | 7 | 7 | 8* | 4* | 5.5* | 9* | 2 | 2 | 7 | | 7 |
| | | | | 1.12 | 6* | | 8 | 2 | 3.5* | 3* | 7 | 7 | 6.5* | 0* | 4.5* | 9* | | | | | |
| | | | | 0.56 | 3.5* | | 8 | 0 | 0* | 1* | 7 | 6 | 3.5* | 0* | 0.5* | 9* | | | | | |
| CH₃ | CH(CH₃)₂ | —CH₂—C≡CH | 4(5)CH₃ | 11.2 | 9 | | 9 | 9 | 8 | 8 | 8 | 9 | 8 | 9 | 9 | 8 | | | | | 9 |
| | | | | 2.24 | 9 | | 8 | | 8 | 8 | 8 | 8 | 8 | 7 | 7 | 9 | | | | | 8 |
| | | | | 1.12 | 9 | | 8 | | 8 | 5 | 7 | 8 | 6 | 6 | 7 | 9 | | | | | 8 |
| | | | | 0.56 | 6 | 8 | 9 | | 8 | 2 | 6 | 7 | 3 | 3 | 2 | 9 | | | | | |
| CH₃ | CH(CH₃)₂ | —C(CH(CH₃)₂)(CH=CH₂)(CH(CH₃)₂) | H | 11.2 | 9 | 8 | 9 | 9 | 8 | 8 | 8 | 9 | 9 | 9 | 9 | 8 | 7 | 7 | 7 | | 8 |
| | | | | 2.24 | 9 | | 9 | | 0 | 7 | 6 | 9 | 8 | 0 | 5 | 8 | 7 | 7 | 6 | | 8 |
| | | | | 1.12 | 9 | | 9 | | 0 | 5 | 5 | 6 | 3 | 0 | 2 | 2 | 6 | 6 | | | |
| CH₃ | CH(CH₃)₂ (+) isomer | —C₂H₅ | H | 11.2 | 8 | 6 | 8 | 9 | 6 | 8 | 8 | 9 | 7 | 6 | 8 | 8 | 9 | 8 | 8 | | 9 |
| | | | | 1.12 | 8 | | 8 | | 5 | 8 | 8 | 9 | 5 | 0 | 0 | 8 | 8 | 8 | 7 | | 9 |
| | | | | 0.56 | 7 | | 7 | | 5 | 7 | 7 | 9 | 2 | 0 | 0 | 8 | | | | | |

TABLE II-continued

Preemergence Herbicidal Activity for Compounds having the Structure:

$$\text{X} - \text{C}_6\text{H}_3 \begin{pmatrix} \text{COOR}_3 \\ \text{C}(=\text{N}-)\text{N(H)}-\text{CR}_1\text{R}_2-\text{C}(=\text{O})- \end{pmatrix}$$

| R₁ | R₂ | Structure R₃ | X | Rate kg per Hectare | PN | SE | MU | PI | RW | MO | TW | VL | BA | CR | FO | WO | CN | CO | SY | RI | JW |
|---|---|---|---|---|---|---|---|---|---|---|---|---|---|---|---|---|---|---|---|---|---|
| CH₃ | CH(CH₃)₂ (−) isomer | —CH₂—C≡CH | H | 0.28 | 7 | | | | 3 | 7 | 5 | 9 | 2 | 0 | 0 | 8 | 7 | 7 | 7 | | 7 |
| | | | | 11.2 | 9 | 9 | 9 | 9 | 8 | 8 | 8 | 8 | 9 | 9 | 9 | 8 | 9 | 8 | 8 | | 8 |
| | | | | 1.12 | 9 | | | | 8 | 8 | 8 | 9 | 8 | 7 | 9 | 9 | 9 | 8 | 8 | | 8 |
| | | | | 0.56 | 9 | | | | 8 | 8 | 8 | 9 | 9 | 6 | 9 | 9 | 9 | 7 | 8 | | 8 |
| | | | | 0.28 | 8 | 8 | | | 6 | 7 | 7 | 8 | 6 | 3 | 8 | 8 | 8 | 6 | 7 | | 7 |
| | | | | 0.14 | 9 | | | | 5 | 7 | 3 | 7 | 3 | 0 | 0 | 7 | 7 | | | | |
| CH₃ | CH(CH₃)₂ (+) isomer | —CH₃—C=CH₂ \| Cl | H | 11.2 | 9 | 8 | 9 | 9 | 8 | 8 | 8 | 9 | 9 | 9 | 9 | 8 | 9 | 8 | 8 | | 8 |
| | | | | 2.24 | 9 | | | | 8 | 8 | 9 | 8 | 8 | 9 | 9 | 8 | 9 | 8 | 8 | | 8 |
| | | | | 1.12 | 9 | | | | 8 | 7 | 8 | 9 | 8 | 9 | 8 | 8 | 8 | 8 | 7 | | 8 |
| | | | | 0.56 | 9 | | | | 8 | 7 | 7 | 8 | 7 | 5 | 8 | 8 | 8 | 6 | 7 | | 8 |
| | | | | 0.28 | 8 | | | | 2 | 7 | 5 | 5 | 5 | 2 | 7 | 7 | 3 | 6 | 6 | | 7 |
| | | | | 0.14 | 6 | | | | 0 | 7 | 3 | 3 | 3 | 0 | 2 | 3 | 2 | 3 | 3 | | |
| | | | | 0.07 | 3 | | | | 0 | 6 | 0 | 2 | 0 | 0 | 0 | 3 | | | | | |
| CH₃ | CH(CH₃)₂ | —CH(CH₃)CH=CHCH₃ | 4(5)CH₃ | 11.2 | 9 | 8 | 9 | 9 | 8 | 8 | 8 | 9 | 8 | 8 | 9 | 8 | 8 | | 7 | | 8 |
| | | | | 2.24 | 9 | | | | 8 | 7 | 8 | 8 | 6 | 6 | 7 | 9 | 5 | 5 | 6 | | 8 |
| | | | | 1.12 | 9 | | | | 6 | 6 | 6 | 6 | 3 | 0 | 2 | 8 | 0 | 2 | 5 | | 3 |
| | | | | 0.56 | 9 | | | | 3 | 2 | 3 | 3 | 0 | 0 | 0 | 7 | | 0 | | | |
| CH₃ | CH(CH₃)₂ | —CH₃ | 3(6)Cl | 11.2 | 0 | 0 | 8 | 9 | 0 | 0 | 7 | 7 | 0 | 0 | 0 | 0 | | | | | |
| CH₃ | CH(CH₃)₂ | —CH₂C≡CH | 3(6)Cl | 11.2 | 7 | 0 | 8 | 8 | 6 | 7 | 7 | 8 | 6 | 0 | 0 | 0 | | | | | |
| CH₃ | CH(CH₃)₂ | —CH₂C≡C—CH₂OH | H | 11.2 | 9 | 8 | 9 | 9 | 8 | 8 | 8 | 8 | 8 | 9 | 9 | 8 | 9 | 8 | 8 | | 8 |
| | | | | 2.24 | 9 | | | | 8 | 8 | 8 | 8 | 8 | 9 | 8 | 8 | 8 | 7 | 8 | | 7 |
| | | | | 1.12 | 9 | | | | 5 | 8 | 7 | 8 | 6 | 7 | 8 | 7 | 7 | 6 | 7 | | 7 |
| | | | | 0.56 | 9 | | | | 0 | 8 | 5 | 5 | 3 | 2 | 7 | 7 | 2 | 3 | 3 | | 3 |
| | | | | 0.28 | 9 | | | | 0 | 8 | 2 | 3 | 2 | 0 | 0 | 3 | | | | | 5 |
| CH₃ | CH(CH₃)₂ | —CH₂—C=CH₂ \| Cl | 3(6)Cl | 11.2 | 0 | 0 | 9 | 9 | 0 | 6 | 7 | 6 | 0 | 0 | 0 | 0 | | | | | |
| CH₃ | CH(CH₃)₂ | —CH(CH₃)₂CH=CH—CH₃ | 3(6)Cl | 11.2 | 0 | 0 | 8 | 9 | 0 | 4 | 7 | 8 | 7 | 0 | 0 | 0 | 5 | 6 | 7 | | |
| CH₃ | CH(CH₃)₂ | —C₂H₅ | 3(6)NO₂ | 11.2 | 5 | 0 | 8 | 8 | 1 | 8 | 7 | 7 | 7 | 7 | 0 | 2 | 0 | 3 | 5 | | |
| CH₃ | C₂H₅ | —CH₃ | H | 11.2 | 9 | 5 | 9 | | 0 | 8 | 8 | 9 | 7 | 0 | 8 | 9 | | | | | |
| | | | | 2.24 | 7 | | | | 0 | 8 | 8 | 9 | 3 | 0 | 3 | 8 | 5 | | | | |
| | | | | 1.12 | 2 | | | | 0 | 7 | 7 | 8 | 0 | 0 | 0 | 7 | 0 | | | | |
| CH₃ | C₂H₅ | —CH₂—C≡CH | H | 11.2 | 9 | 8 | 9 | 9 | 3 | 8 | 8 | 9 | 8 | 8 | 8 | 9 | 7 | 7 | 7 | | 9 |
| | | | | 2.24 | 9 | | | | 0 | 8 | 8 | 8 | 7 | 6 | 9 | 8 | 3 | 5 | 6 | | 9 |
| | | | | 1.12 | 9 | | | | 0 | 8 | 6 | 8 | 3 | 2 | 3 | 6 | 3 | 5 | 6 | | 8 |

TABLE II-continued

Preemergence Herbicidal Activity for Compounds having the Structure:

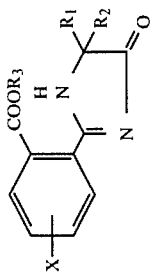

| R$_1$ | R$_2$ | Structure R$_3$ | X | Rate kg per Hectare | PN | SE | MU | PI | RW | MO | TW | VL | BA | CR | FO | WO | CN | CO | SY | RI | JW |
|---|---|---|---|---|---|---|---|---|---|---|---|---|---|---|---|---|---|---|---|---|---|
| CH$_3$ | C$_2$H$_5$ |  |  | 0.56 | 3 |  |  |  | 0 | 7 | 5 | 5 | 0 | 0 | 0 | 0 | 0 | 2 | 2 |  | 8 |
|  |  | —CH$_2$—C=CH$_2$ <br> \|<br> Cl | H | 11.2 <br> 2.24 <br> 1.12 <br> 0.56 <br> 0.28 | 9 <br> 9 <br> 7 <br> 5 <br> 2 | 7 |  | 9 | 8 <br> 8 <br> 0 <br> 0 <br> 0 | 8 <br> 8 <br> 8 <br> 0 <br> 3 | 9 <br> 8 <br> 6 <br> 0 <br> 0 | 9 <br> 8 <br> 2 <br> 1 <br> 0 | 9 <br> 6 <br> 3 <br> 0 <br> 0 | 9 <br> 6 <br> 0 <br> 0 <br> 0 | 9 <br> 8 <br> 6 <br> 7 <br> 0 | 8 <br> 8 <br> 6 <br> 2 <br> 0 | 7 <br> 3 <br> 1 <br> 0 | 5 <br> 5 <br> 3 <br> 1 | 6 <br> 3 <br> 2 <br> 0 |  | 8 <br> 8 <br> 7 <br> 7 |
| CH$_3$ | CH(CH$_3$)$_2$ | —CH$_2$—C=CHCl <br> \|<br> Cl | H | 11.2 <br> 2.24 <br> 1.12 <br> 0.56 <br> 0.28 | 9 <br> 9 <br> 9 <br> 9 <br> 8 | 8 |  | 9 | 8 <br> 8 <br> 2 <br> 0 <br> 0 | 8 <br> 8 <br> 8 <br> 6 <br> 2 | 9 <br> 8 <br> 7 <br> 6 <br> 5 | 9 <br> 9 <br> 8 <br> 7 <br> 6 | 9 <br> 9 <br> 8 <br> 3 <br> 0 | 9 <br> 9 <br> 5 <br> 2 <br> 0 | 9 <br> 9 <br> 8 <br> 5 <br> 0 | 8 <br> 8 <br> 7 <br> 3 <br> 0 | 8 <br> 7 <br> 7 <br> 1 | 8 <br> 7 <br> 6 <br> 5 | 8 <br> 8 <br> 7 <br> 7 |  | 8 <br> 8 <br> 8 <br> 8 |
| CH$_3$ | C$_2$H$_5$ | CH$_3$ <br> \| <br> —CH—CH=CH—CH$_3$ | H | 11.2 <br> 2.24 <br> 1.12 | 9 <br> 9 <br> 9 | 6 |  | 9 | 0 <br> 0 <br> 0 | 8 <br> 8 <br> 7 | 8 <br> 8 <br> 5 | 9 <br> 8 <br> 2 | 8 <br> 5 <br> 2 | 7 <br> 2 <br> 0 | 8 <br> 5 <br> 2 | 8 <br> 3 <br> 0 | 7 <br> 2 | 7 <br> 5 | 7 <br> 5 |  | 8 <br> 8 |
| CH$_3$ | CH(CH$_3$)$_2$ | —CH$_2$—C=CH$_2$ <br> \|<br> Cl | 3(6)NO$_2$ | 11.2 | 5 | 0 | 8 | 8 | 6 | 7 | 8 | 8 | 5 | 0 | 6 | 5 |  |  |  |  |  |
| CH$_3$ | CH(CH$_3$)$_2$ | CH$_3$ <br> \| <br> —C—CH=CH$_2$ <br> \| <br> C$_2$H$_5$ | H | 11.2 <br> 2.24 <br> 1.12 <br> 0.56 <br> 0.28 <br> 0.14 | 9 <br> 9 <br> 9 <br> 8 <br> 9 <br> 9 | 7 |  | 9 | 8 <br> 8 <br> 0 <br> 0 <br> 0 <br> 0 | 7 <br> 8 <br> 8 <br> 7 <br> 7 <br> 2 | 8 <br> 8 <br> 7 <br> 3 <br> 5 <br> 0 | 9 <br> 9 <br> 7 <br> 7 <br> 3 <br> 1 | 8 <br> 9 <br> 7 <br> 3 <br> 0 <br> 0 | 9 <br> 8 <br> 7 <br> 0 <br> 0 <br> 0 | 8 <br> 9 <br> 9 <br> 8 <br> 8 <br> 0 | 8 <br> 8 <br> 6 <br> 5 <br> 3 <br> 0 | 9 <br> 8 <br> 7 <br> 6 <br> 6 | 8 <br> 7 <br> 5 <br> 3 <br> 2 | 8 <br> 6 <br> 5 <br> 2 <br> 1 |  | 8 <br> 8 <br> 8 <br> 8 <br> 3 |
| CH$_3$ | C$_2$H$_5$ | CH$_3$ <br> \| <br> —C—CH=CH$_2$ <br> \| <br> CH$_3$ | H | 11.2 <br> 2.24 <br> 1.12 <br> 0.56 | 9 <br> 9 <br> 9 <br> 7 | 0 |  | 8 | 0 <br> 0 <br> 0 <br> 0 | 8 <br> 8 <br> 7 <br> 5 | 8 <br> 8 <br> 7 <br> 3 | 8 <br> 9 <br> 7 <br> 1 | 7 <br> 7 <br> 2 <br> 0 | 8 <br> 5 <br> 1 <br> 0 | 8 <br> 9 <br> 6 <br> 0 | 8 <br> 5 <br> 2 <br> 0 | 8 <br> 5 <br> 1 | 8 <br> 6 <br> 2 | 8 <br> 7 <br> 5 |  | 8 <br> 8 <br> 0 |
| CH$_3$ | CH(CH$_3$)$_2$ | CH(CH$_3$)$_2$ <br> \| <br> —C—C≡CH <br> \| <br> CH(CH$_3$)$_2$ | H | 11.2 <br> 2.24 <br> 1.12 <br> 0.56 | 9 <br> 7 <br> 3 <br> 0 | 9 |  | 9 | 8 <br> 0 <br> 0 <br> 0 | 8 <br> 7 <br> 0 <br> 3 | 8 <br> 8 <br> 6 <br> 5 | 9 <br> 8 <br> 8 | 8 <br> 6 <br> 5 <br> 3 | 8 <br> 7 <br> 6 <br> 0 | 8 <br> 8 <br> 7 <br> 6 | 7 <br> 3 <br> 0 <br> 0 | 3 <br> 0 <br> 0 | 5 <br> 3 <br> 0 <br> 1 | 5 <br> 2 <br> 1 |  | 9 <br> 8 <br> 7 |

TABLE II-continued

Preemergence Herbicidal Activity for Compounds having the Structure:

$$\text{2-}(COOR_3)\text{-}C_6H_3X\text{-}C(=N\text{-}N=CH_2)\text{-}NH\text{-}CR_1R_2\text{-}CHO$$

| Structure | | | Rate kg per | Plant Species | | | | | | | | | | | | | | | |
|---|---|---|---|---|---|---|---|---|---|---|---|---|---|---|---|---|---|---|---|
| R₁ | R₂ | R₃ | X | Hectare | PN | SE | MU | PI | RW | MO | TW | VL | BA | CR | FO | WO | CN | CO | SY | RI | JW |
| CH₃ | CH(CH₃)₂ | —C₂H₅ | 4(5)Cl | 11.2 | 8 | 1 | 8 | 9 | 8 | 8 | 7 | 9 | 6 | 3 | 7 | 7 | 0 | 6 | 3 | | |
| | | | | 2.24 | 1 | | | | 2 | 7 | 5 | 6 | 3 | 1 | 3 | 8 | 0 | 3 | 0 | | |
| | | | | 1.12 | | | | | | | | | | | | | | | | | |
| C₂H₅ | CH(CH₃)₂ | —CH₃ | H | 11.2 | 3 | 0 | 8 | 8 | 0 | 5 | 5 | 2 | 0 | 0 | 0 | 8 | | | | | |
| C₂H₅ | CH(CH₃)₂ | —CH₂—C≡CH | H | 11.2 | 7 | 0 | 8 | 9 | 0 | 6 | 3 | 6 | 1 | 1 | 1 | 1 | | | | | |
| C₂H₅ | CH(CH₃)₂ | —CH₂—C(Cl)=CH₂ | H | 11.2 | 3 | 0 | 8 | 9 | 0 | 8 | 8 | 8 | 7 | 6 | 8 | 8 | | | | | |
| CH₃ | CH(CH₃)₂ | H | 4(5)Cl | 11.2 | 9 | 8 | | 9 | 8 | 8 | 8 | 9 | 9 | 9 | 9 | 9 | 8 | 8 | 7 | | 8 |
| | | | | 2.24 | 9 | | | | 8 | 8 | 8 | 8 | 8 | 8 | 8 | 8 | 8 | 8 | 7 | | 8 |
| | | | | 1.12 | 9 | | | | 6 | 8 | 7 | 8 | 6 | 3 | 8 | 8 | 7 | 7 | 7 | | 8 |
| | | | | 0.56 | 9 | | | | 6 | 7 | 7 | 7 | 5 | 3 | 5 | 6 | 5 | 6 | 6 | | 8 |
| | | | | 0.28 | 9 | | | | 8 | 5 | 8 | 6 | 3 | 1 | 2 | 5 | 3 | 3 | 5 | | 5 |
| | | | | 0.14 | 3 | | | | 8 | 5 | 3 | 9 | 3 | 3 | 2 | 3 | 3 | 3 | 3 | | |
| CH₃ | CH(CH₃)₂ | —CH₂—C≡CH | 4(5)Cl | 11.2 | 9 | 8 | | 9 | 8 | 8 | 8 | | 8 | 8 | 9 | 8 | 6 | 8 | 5 | | 8 |
| | | | | 2.24 | 8 | | | | 8 | 8 | 8 | | 8 | 7 | 7 | 8 | 1 | 0 | 5 | | 8 |
| | | | | 1.12 | 6 | | | | 7 | 8 | 5 | | 7 | 5 | 7 | 8 | 0 | 1 | 1 | | 8 |
| | | | | 0.56 | 5 | | | | 7 | 8 | 2 | | 5 | 0 | 6 | 7 | 0 | 0 | 1 | | 8 |
| | | | | 0.28 | 3 | | | | 7 | 7 | 0 | | 2 | 0 | 3 | 7 | 0 | 0 | 1 | | |
| CH₃ | CH(CH₃)₂ | —CH(CH₃)—CH=CHCH₃ | 4(5)Cl | 11.2 | 9 | 8 | | 8 | 8 | 8 | 8 | 8 | 8 | 8 | 8 | 8 | 6 | 5 | 6 | | 7 |
| | | | | 2.24 | 9 | | | | 8 | 7 | 2 | 6 | 7 | 7 | 7 | 7 | 2 | 1 | 5 | | 3 |
| | | | | 1.12 | 6 | | | | 7 | 3 | 0 | | 6 | 0 | 5 | 2 | 2 | 0 | 3 | | 0 |
| | | | | 0.56 | 2 | | | | 0 | 5 | 0 | | 6 | 0 | 2 | 2 | 0 | 0 | 0 | | |
| CH₃ | C₂H₅ | H | H | 11.2 | 9 | 8 | | 8 | 8 | 8 | 8 | 8 | 8 | 8 | 9 | 8 | 8 | 9 | 9 | | 8 |
| | | | | 2.24 | 9 | | | | 0 | 8 | 8 | | 9 | 9 | 9 | 8 | 7 | 9 | 8 | | 8 |
| | | | | 1.12 | 9 | | | | 0 | 8 | 7 | | 1 | 1 | 3 | 5 | 3 | 3 | 8 | | 8 |
| | | | | 0.56 | 9 | | | | 0 | 7 | 5 | | 1 | 1 | 5 | 2 | 3 | 3 | 7 | | 7 |
| | | | | 0.28 | 9 | | | | 3 | 8 | 8 | 8 | 7 | 8 | 5 | 5 | 3 | 6 | 5 | | 7 |
| C₂H₅ | CH(CH₃)₂ | H | H | 11.2 | 8 | 0 | 8 | 8 | 0 | 8 | 2 | 7 | 3 | 2 | 2 | 0 | 3 | 5 | 2 | | 1 |
| | | | | 2.24 | 9 | | | | 0 | 6 | 0 | 0 | 0 | 0 | 7 | 0 | 3 | 2 | 2 | | 0 |
| | | | | 1.12 | 9 | | | | 9 | 3 | 0 | 0 | 0 | 0 | 0 | 0 | 1 | | | | |
| CH₃ | CH(CH₃)₂ | H | 3(6)Cl | 11.2 | 9 | 8 | | 8 | 8 | 8 | 8 | 8 | 9 | 8 | 9 | 8 | 9 | 9 | 8 | | 8 |
| | | | | 2.24 | 9 | | | | 9 | 8 | 7 | | 8 | 9 | 8 | 7 | 7 | 8 | 8 | | 8 |
| | | | | 1.12 | 9 | | | | 8 | 8 | 3 | | 7 | 6 | 3 | 7 | | | | | |

TABLE II-continued
Preemergence Herbicidal Activity for Compounds having the Structure:
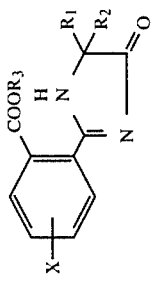
| Structure | | | | | | | | | | | | | | | | | Plant Species | | | | | | | |
|---|---|---|---|---|---|---|---|---|---|---|---|---|---|---|---|---|---|---|---|---|---|---|---|---|
| $R_1$ | $R_2$ | $R_3$ | X | Rate kg per Hectare | PN | SE | MU | PI | RW | MO | TW | VL | BA | CR | FO | WO | CN | CO | SY | RI | JW |
| $CH_3$ | $CH(CH_3)_2$ | $-CH_2-C=CH_2$ <br> \| <br> Cl | 4(5)Cl | 0.56 | 9 | | | | 7 | 8 | 2 | 9 | 3 | 1 | 1 | 2 | 6 | 8 | 8 | | 7 |
| | | | | 0.28 | 9 | | | | 7 | 8 | 2 | 7 | 1 | 0 | 0 | 2 | 2 | 8 | 7 | | 7 |
| | | | | 11.2 | 9 | 8 | 8 | 9 | 8 | 8 | 8 | 9 | 8 | 8 | 8 | 8 | 7 | 8 | 7 | | 8 |
| | | | | 2.24 | 9 | | | | 8 | 8 | 7 | 7 | 9 | 9 | 8 | 8 | 2 | 5 | 5 | | 8 |
| | | | | 1.12 | 9 | | | | | 8 | 5 | 6 | 8 | 8 | 7 | 8 | 0 | 6 | 2 | | 8 |
| | | | | 0.56 | 8 | | | | | 7 | 1 | 0 | 7 | 5 | 6 | 5 | 0 | 3 | 2 | | 8 |
| | | | | 0.28 | 5 | | | | | 7 | 0 | 0 | 5 | 5 | 5 | 2 | 0 | 3 | 1 | | 7 |
| | | | | 0.13 | 0 | | | | 7 | 3 | 0 | 0 | 0 | 3 | 3 | 0 | | | | | |
| $CH_3$ | $CH(CH_3)_2$ | $CH_2=CH_2$ <br> \| <br> $-CH-CH\equiv CH$ | H | 11.2 | 9 | 9 | | | 8 | 8 | 8 | 8 | 9 | 8 | 9 | 8 | 9 | 8 | 8 | | 8 |
| | | | | 2.24 | 9 | | | | | 8 | 8 | 9 | 9 | 9 | 9 | 8 | 7 | 8 | 7 | | 8 |
| | | | | 1.12 | 9 | | | | 8 | 8 | 8 | 8 | 9 | 8 | 9 | 8 | 7 | 8 | 7 | | 8 |
| | | | | 0.56 | 9 | | | | 8 | 7 | 7 | 7 | 7 | 8 | 8 | 6 | 5 | 8 | 7 | | 8 |
| | | | | 0.28 | 9 | | | | | 7 | 5 | 7 | 7 | 8 | 7 | 5 | 2 | 8 | 6 | | 8 |
| | | | | 0.14 | 9 | | | | | 5 | 5 | 6 | 7 | 8 | 6 | 3 | 2 | 7 | 2 | | 7 |
| | | | | 0.07 | | | | | | | | | | | | | | | | | |
| $CH_3$ | $CH(CH_3)_2$ | $CH_3$ <br> \| <br> $-C-CH=CH_2$ <br> \| <br> $CH_3$ | 4(5)Cl | 11.2 | 9 | 7 | 8 | 8 | 8 | 8 | 8 | 8 | 8 | 8 | 8 | 8 | 8 | 8 | 8 | | 8 |
| | | | | 2.24 | 9 | | | | | 8 | 8 | 8 | 8 | 8 | 8 | 8 | 6 | 9 | 7 | | 8 |
| | | | | 1.12 | 9 | | | | | 5 | 5 | 5 | 7 | 8 | 7 | 6 | 3 | 8 | 7 | | 7 |
| | | | | 0.56 | 8 | | | | | 8 | 5 | 3 | 7 | 7 | 6 | 2 | 3 | 5 | 7 | | 7 |
| | | | | 0.28 | 8 | | | | 0 | 7 | 1 | 1 | 0 | 1 | 5 | 0 | 2 | 5 | 6 | | 5 |
*= AVERAGE OF TWO OR MORE TESTS.

EXAMPLE 8

Selective Postemergence Herbicidal Activity

The selective postemergence herbicidal activity of the compounds of the invention is demonstrated by the following tests, wherein sorghum [*Sorghum bicolor* (L) Woeuch], spring wheat (*Triticum acstivum*, cv. Auza) and barley (*Hordcum vulgare*, cv. Steptoe) plants are treated with test compounds dispersed in aqueous acetone mixtures. In these tests, the procedure described in Example 6 is followed, and the treated plants are examined and rated according to the rating system set forth in Example 6.

The data obtained are reported in Table III below.

TABLE III

SELECTIVE POSTEMERGENCE HERBICIDAL ACTIVITY OF COMPOUNDS HAVING THE STRUCTURE:

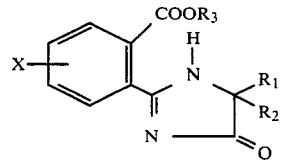

| STRUCTURE | | | | Rate kg per | PLANT SPECIES | | |
|---|---|---|---|---|---|---|---|
| $R_1$ | $R_2$ | $R_3$ | X | Hectare | Sorghum | Auza | Steptoe |
| $-CH_3$ | $-CH(CH_3)_2$ | $-CH_2CH_2OCH_3$ | H | 2.24 | 2 | 5 | 2 |
| | | | | 1.12 | 0 | 5 | 0 |
| | | | | 0.56 | 0 | 0 | 0 |
| $-CH_3$ | $-CH(CH_3)_2$ | $-C(CH_3)(C_2H_5)(CH_3)$ | H | 2.24 | 2 | 5 | 0 |
| | | | | 1.12 | 0 | 3 | 0 |
| | | | | 0.56 | 0 | 5 | 0 |
| $-CH_3$ | $-CH(CH_3)_2$ | $-CH_2CH_2OC_2H_5$ | H | 2.24 | 3 | 2 | 2 |
| | | | | 1.12 | 0 | 2 | 2 |
| | | | | 0.56 | 0 | 0 | 0 |
| $-CH_3$ | $-CH(CH_3)_2$ | $-CH(CH_3)$-cyclopropyl | H | 2.24 | 3 | 6 | 3 |
| | | | | 1.12 | 0 | 5 | 0 |
| | | | | 0.56 | 0 | 3 | 0 |
| $-CH_3$ | $-CH(CH_3)_2$ | $-CH_2-C\equiv C-C_7H_{15}-n$ | H | 2.24 | 2 | 3 | 0 |
| | | | | 1.12 | 0 | 2 | 0 |
| | | | | 0.56 | 0 | 2 | 0 |
| $-CH_3$ | $-CH(CH_3)_2$ | 4-isopropylcyclohexyl-CH$_3$ | H | 2.24 | 0 | 3 | 2 |
| | | | | 1.12 | 0 | 0 | 0 |
| | | | | 0.56 | 0 | 0 | 0 |
| $-CH_3$ | $-CH(CH_3)_2$ | $-CH_3$ | 4(5)CH$_3$ | 2.24 | 2 | 1 | 0 |
| | | | | 1.12 | 2 | 0 | 0 |
| | | | | 0.56 | 0 | 0 | 0 |
| $-CH_3$ | $-CH(CH_3)_2$ (+) isomer | $-C_2H_5$ | H | 2.24 | 2 | 9 | 2 |
| | | | | 1.12 | 1 | 8 | 0 |
| | | | | 0.56 | 0 | 3 | 0 |
| $-CH_3$ | $-CH(CH_3)_2$ | $-CH_2-C\equiv CH$ | 3(6)Cl | 2.24 | 2 | 0 | 0 |
| | | | | 1.12 | 0 | 0 | 0 |
| | | | | 0.56 | 0 | 0 | 0 |
| $-CH_3$ | $-CH(CH_3)_2$ | $-C_2H_5$ | 3(6)NO$_2$ | 2.24 | 0 | 0 | 0 |
| | | | | 1.12 | 0 | 0 | 0 |
| | | | | 0.56 | 0 | 0 | 0 |
| $-CH_3$ | $-C_2H_5$ | $-CH_3$ | H | 2.24 | 0 | 2 | 0 |
| | | | | 1.12 | 0 | 3 | 0 |
| | | | | 0.56 | 0 | 0 | 0 |
| $-CH_3$ | $-CH(CH_3)_2$ | $-CH_2-C(Cl)=CH_2$ | 3(6)NO$_2$ | 2.24 | 0 | 0 | 6 |
| | | | | 1.12 | 0 | 0 | 7 |
| | | | | 0.56 | 0 | 0 | 1 |
| $-CH_3$ | $-CH(CH_3)_2$ | $-C_2H_5$ | 4(5)Cl | 2.24 | 0 | 0 | 0 |
| | | | | 1.12 | 0 | 0 | 0 |
| | | | | 0.56 | 0 | 0 | 0 |

TABLE III-continued
SELECTIVE POSTEMERGENCE HERBICIDAL ACTIVITY OF COMPOUNDS HAVING THE STRUCTURE:

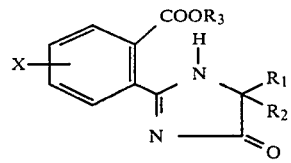

| STRUCTURE | | | | Rate kg per | PLANT SPECIES | | |
|---|---|---|---|---|---|---|---|
| $R_1$ | $R_2$ | $R_3$ | X | Hectare | Sorghum | Auza | Steptoe |
| $-CH_3$ | $-CH(CH_3)_2$ | $\begin{array}{c}CH_3\\|\\-CH-CH=CHCH_3\end{array}$ | 4(5)Cl | 2.24 | 6 | 0 | 0 |
| | | | | 1.12 | 3 | 0 | 0 |
| | | | | 0.56 | 0 | 0 | 0 |

EXAMPLE 9

Selective Preemergence Herbicidal Activity

By the procedure described in Example 7, the selective preemergence herbicidal activity of the compounds of the invention is evaluated using sorghum [*Sorghum bicolor* (L) Moeuch], spring wheat (*Triticum acstivum*, cv. Auza) and barley (*Hordeum vulgare*, cv. Steptoe). At termination the tests are rated according to the rating system set forth in Example 6.

The data obtained are reported in Table IV below.

TABLE IV
SELECTIVE PREEMERGENCE HERBICIDAL ACTIVITY OF COMPOUNDS HAVING THE STRUCTURE

| STRUCTURE | | | | Rate kg per | PLANT SPECIES | | |
|---|---|---|---|---|---|---|---|
| $R_1$ | $R_2$ | $R_3$ | X | Hectare | Sorghum | Auza | Steptoe |
| $-CH_3$ | $-CH(CH_3)_2$ | $-CH_2C(CH_3)_3$ | H | 2.24 | 0 | 2 | 0 |
| | | | | 1.12 | 0 | 0 | 0 |
| | | | | 0.56 | 0 | 0 | 0 |
| $-CH_3$ | $-CH(CH_3)_2$ | $-CH_2CH_2OCH_3$ | H | 2.24 | 0 | 7 | 2 |
| | | | | 1.12 | 0 | 3 | 0 |
| | | | | 0.56 | 0 | 0 | 0 |
| $-CH_3$ | $-CH(CH_3)_2$ | $-C_6H_{13}-n$ | H | 2.24 | 3 | 2 | 0 |
| | | | | 1.12 | 0 | 0 | 0 |
| | | | | 0.56 | 0 | 0 | 0 |
| $-CH_3$ | $-CH(CH_3)_2$ | $\begin{array}{c}CH_3\\|\\-C-C_2H_5\\|\\CH_3\end{array}$ | H | 2.24 | 2 | 5 | 2 |
| | | | | 1.12 | 0 | 3 | 0 |
| | | | | 0.56 | 0 | 0 | 0 |
| $-CH_3$ | $-CH(CH_3)_2$ | $-CH_2CH_2OC_2H_5$ | H | 2.24 | 2 | 8 | 7 |
| | | | | 1.12 | 0 | 5 | 0 |
| | | | | 0.56 | 0 | 3 | 0 |
| $-CH_3$ | $-CH(CH_3)_2$ | $-CH_2CH=CH-C_6H_5$ | H | 2.24 | 3 | 7 | 3 |
| | | | | 1.12 | 2 | 0 | 0 |
| | | | | 0.56 | 0 | 0 | 0 |
| $-CH_3$ | $-CH(CH_3)_2$ | $-CH_3$ | 4(5)$CH_3$ | 2.24 | 8 | 2 | 3 |
| | | | | 1.12 | 8 | 0 | 0 |
| | | | | 0.56 | 2 | 0 | 0 |
| $-CH_3$ | $-CH(CH_3)_2$ | $-CH_2-CH_2-$ | H | 2.24 | 0 | 6 | 3 |
| | | | | 1.12 | 0 | 0 | 0 |
| | | | | 0.56 | 0 | 0 | 0 |
| $-CH_3$ | $-C_2H_5$ | $-CH_3$ | H | 2.24 | 2 | 2 | 2 |
| | | | | 1.12 | 0 | 0 | 0 |
| | | | | 0.56 | 0 | 0 | 0 |
| $-CH_3$ | $-CH(CH_3)_2$ | $-C_2H_5$ | 4(5)Cl | 2.24 | 0 | 7 | 0 |
| | | | | 1.12 | 0 | 0 | 0 |
| | | | | 0.56 | 0 | 0 | 0 |

TABLE IV-continued

SELECTIVE PREEMERGENCE HERBICIDAL ACTIVITY
OF COMPOUNDS HAVING THE STRUCTURE

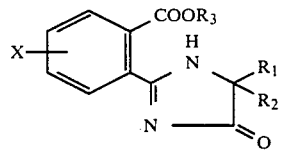

| STRUCTURE | | | | Rate kg per | PLANT SPECIES | | |
|---|---|---|---|---|---|---|---|
| $R_1$ | $R_2$ | $R_3$ | | X | Hectare | Sorghum | Auza | Steptoe |
| —$CH_3$ | —$CH(CH_3)_2$ | $CH(CH_3)_2$<br>\|<br>—C—C≡CH<br>\|<br>$CH(CH_3)_2$ | H | 2.24<br>1.12<br>0.56 | 5<br>0<br>0 | 6<br>3<br>0 | 2<br>0<br>0 |
| —$CH_3$ | —$CH(CH_3)_2$ | $CH_3$<br>\|<br>—CH—CH=$CHCH_3$ | 4(5)Cl | 2.24<br>1.12<br>0.56 | 8<br>2<br>1 | 7<br>5<br>2 | 2<br>0<br>0 |

I claim:

1. A method for the preparation of a compound having the formula:

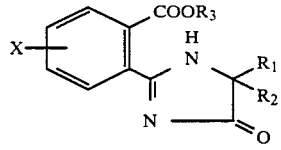

wherein X is hydrogen, alkyl $C_1$–$C_3$, halogen or nitro; $R_1$ is alkyl $C_1$–$C_4$; $R_2$ is alkyl $C_1$–$C_6$, cycloalkyl $C_3$–$C_6$, alkenyl $C_2$–$C_4$, phenyl, halophenyl or benzyl or when $R_1$ and $R_2$ are taken together with the carbon to which they are attached they may represent cycloalkyl $C_3$–$C_6$ optionally substituted with methyl; $R_3$ is, alkyl $C_1$–$C_{12}$ optionally substituted with one $C_1$–$C_3$ alkoxy group or one $C_3$–$C_6$ cycloalkyl group or one phenyl group or one furyl group, alkenyl $C_3$–$C_5$ optionally substituted with one or two $C_1$–$C_3$ alkyl group(s) or one phenyl group or with one to two halogen substituent(s) alkynyl $C_3$–$C_5$ optionally substituted with one or two $C_1$–$C_3$ alkyl group(s) or one phenyl group or with one to two halogen substituent(s), benzyl, cyclohexenylmethyl, ethynylcyclohexyl, ethynylalkyl or pentadienyl, cycloalkyl, $C_3$–$C_6$ optionally substituted with one or two $C_1$–$C_3$ alkyl group(s); and when $R_1$ and $R_2$ are not the same the optical isomers thereof, and the isomeric mixtures thereof; comprising, reacting a compound having the formula:

wherein X, $R_1$ and $R_2$ are as described above, which an alcohol having the formula: $R_3OH$ where $R_3$ is described above, in the presence of an alkali metal or alkali metal hydride and at a temperature between about 20° C. and 50° C.

2. A method according to claim 1, wherein the ratio of alcohol to imidazoisoindoledione is from 1.1 to 1.0 to 5.0 to 1.0 and the reaction is conducted under a blanket of inert gas.

3. A method according to claim 1, wherein a non-protic solvent is added to the reaction mixture of imidazoisoindoledione, alcohol and alkali metal or alkali metal hydride, such that the ratio of non-protic solvent to alcohol does not exceed 4 to 1 and the reaction is conducted under a blanket of inert gas.

* * * * *